United States Patent
Kozyavkin et al.

(10) Patent No.: US 6,548,251 B1
(45) Date of Patent: Apr. 15, 2003

(54) INHIBITION OF MOLECULAR AND BIOLOGICAL PROCESSES USING MODIFIED OLIGONUCLEOTIDES

(75) Inventors: Sergei A. Kozyavkin, Germantown, MD (US); Andrei G. Malykh, Germantown, MD (US); Nikolai N. Polouchine, Montgomery Village, MD (US); Alexei I. Slesarev, Germantown, MD (US)

(73) Assignee: Fidelity Systems, Inc., Gaithersburg, MD (US)

( * ) Notice: Subject to any disclaimer, the term of this patent is extended or adjusted under 35 U.S.C. 154(b) by 0 days.

(21) Appl. No.: 09/655,804

(22) Filed: Sep. 5, 2000

(51) Int. Cl.$^7$ .............. C12Q 1/68; C12P 19/34; A61K 48/00

(52) U.S. Cl. ............. 435/6; 435/91.1; 435/91.2; 514/44; 536/23.1; 536/24.2; 536/24.3; 536/24.33; 536/24.5

(58) Field of Search .............. 536/23.1, 25.3, 536/25.31, 23.5, 24.3, 24.33, 24.2, 24.5; 435/6, 91.1, 91.2; 514/44

(56) References Cited

U.S. PATENT DOCUMENTS

| | | | |
|---|---|---|---|
| 4,358,535 A | 11/1982 | Falkow et al. | |
| 4,605,735 A | 8/1986 | Miyoshi et al. | |
| 4,665,184 A | 5/1987 | Dervan et al. | |
| 4,683,202 A | 7/1987 | Mullis | |
| 4,729,947 A | 3/1988 | Middendorf et al. | |
| 4,795,700 A | 1/1989 | Dervan et al. | |
| 4,855,225 A | 8/1989 | Fung et al. | |
| 4,889,818 A | 12/1989 | Gelfand et al. | |
| 4,962,020 A | 10/1990 | Tabor et al. | |
| 5,112,962 A | 5/1992 | Letsinger et al. | |
| 5,124,246 A | 6/1992 | Urdea et al. | |
| 5,241,060 A | 8/1993 | Engelhardt et al. | ........ 536/27 |
| 5,348,853 A | 9/1994 | Wang et al. | |
| 5,466,786 A | 11/1995 | Buhr et al. | |
| 5,547,835 A | 8/1996 | Koster | |
| 5,565,340 A | 10/1996 | Chenchik et al. | |
| 5,567,583 A | 10/1996 | Wang et al. | |
| 5,576,427 A | 11/1996 | Cook et al. | |
| 5,614,365 A | 3/1997 | Tabor et al. | |
| 5,681,702 A | 10/1997 | Collins et al. | |
| 5,712,386 A | 1/1998 | Wang et al. | |
| 5,814,492 A | 9/1998 | Carrino et al. | |
| 5,849,497 A | 12/1998 | Steinman | |
| 5,852,188 A | 12/1998 | Cook | |
| 5,863,727 A | 1/1999 | Lee et al. | |
| 5,888,819 A | 3/1999 | Goelet et al. | |
| 5,902,879 A | * 5/1999 | Polouchine | |
| 5,945,526 A | 8/1999 | Lee et al. | |
| 6,001,611 A | * 12/1999 | Will | |
| 6,033,851 A | 3/2000 | Yamane | |
| 6,033,854 A | 3/2000 | Kurnit et al. | |
| 6,057,134 A | 5/2000 | Lader et al. | |
| 6,107,061 A | 8/2000 | Johnson | |

OTHER PUBLICATIONS

V. Efimov, "Recent Developments in the Synthesis of Oligonucleotides, Their Analogues and Conjugates", *Nucleic Acids Symposium*, (Aug. 6–11, 1995).

N. Polushin, "Synthesis of Functionally Modified Oligonucleotides Through 2'–Methoxyoxalamide–2'Deoxyuridine Containing Precursors", *Nucleic Acids Symposium*, (Aug. 6–11, 1995).

N. Polushin, "Synthesis of Functionally Modified Oligonucleotides from Methoxyoxalamido Precursors", *Tetrahedron Letters*, vol. 37, No. 19, pp. 3231–3234, (1996).

N. Polushin et al., "Synthesis of Oligonucleotides Containing 2'–Azido– and 2'–Amino–2'–deoxyuridine Using Phosphotriester Chemistry", *Tetrahedron Letters*, vol. 37, No. 19, pp. 3227–3230, (1996).

N. Herbert et al., "Synthesis of N–Substituted Hydroxyprolinol Phosphoramidites for the Preparation of Combinatorial Libraries", *Tetrahedron Letters*, vol. 35, No. 51, pp. 9509–9512, (1994).

P. Davis et al., "Drug Leads from Combinatorial Phosphodiester Libraries", *J. Med. Chem*, vol. 38, pp. 4363–4366, (1995).

A. MacMillan et al., "Synthesis of Functionally Tethered Oligodeoxynucleotides by the Convertible Nucleoside Approach", *J. Org. Chem*, vol. 55, pp. 5931–5933, (1990).

L. Beigelman et al., "Synthesis of 2'–modified Nucleotides and their Incorporation into Hammerhead Ribozymes", *Nucleic Acids Research*, vol. 23, No. 21, pp. 4434–4442, (1995).

N. Polushin et al., "Synthesis and Characterization of Imidazoyl–Linked Synthons and 3'–Conjugated Thymidine Derivatives", *Journal of Organic Chemistry*, vol. 58, pp. 4606–4613, (1993).

R. Alul et al., "Oxalyl–CPG: A Labile Support for Synthesis of Sensitive Oligonucleotide–Derivatives", *Nucleic Acids Research*, vol. 19, No. 7, pp. 1527–1532, (1991).

A. MacMillan et al., "Engineering Tethered DNA Molecules by the Convertible Nucleoside Approach", *Tetrahedron Letters*, vol. 47, No. 14/15, pp. 2603–1616, (1991).

(List continued on next page.)

*Primary Examiner*—Carla J. Myers
(74) *Attorney, Agent, or Firm*—Oliff & Berridge, PLC

(57) ABSTRACT

A method of inhibiting at least one molecular process in a sample, comprising administering to the sample an oligonucleotide or polynucleotide containing at least one monomeric unit having formula (I):

$$A-X_n \qquad (I)$$

wherein A is an organic moiety, n is at least 1, and each X is independently selected from the group consisting of —NRCOCONu, —NHCOCR$_2$CR$_2$CONu, —NHCOCR=CRCONu, and —NHCOSSCONu, wherein each R independently represents H or a substituted or unsubstituted alkyl group, and Nu represents a nucleophile, or a salt of the compound.

22 Claims, No Drawings

OTHER PUBLICATIONS

A. Ferentz et al., "Aminolysis of 2'–Deoxyinosine Aryl Ethers: Nucleoside Model Studies for the Synthesis of Functionally Tethered Oligonucleotides", *Nucleosides & Nucleotides*, vol. 11, No. 10, pp. 1749–1763, (1992).

F. Benseler et al., "Synthesis of Suitably–protected Phosphoramidites of 2'–Fluoro–2'–Deoxyguanosine and 2–'Amino–2'–Deoxyguanosine for Incorporation into Oligoribonucleotides", *Nucleosides & Nucleotides*, vol. 11, No. 7, pp. 1333–1351, (1992).

I. Smirnov et al., "Sequencing Oligonucleotides by Exonuclease Digestion and Delayed Extraction Matrix–Assisted Laser Desorption Ionization Time–of–Flight Mass Spectrometry", *Analytical Biochemistry*, vol. 288, pp. 19–25, (1996).

J. Goodchild, "Conjugates of Oligonucleotides and Modified Oligonucleotides: A Review of Their Synthesis and Properties", *Perspectives in Bioconjugate Chemistry*, pp. 77–99, (1993).

V. Efimov et al., "New Activators for the Phosphoramidite Oligonucleotide Synthesis", *Bioorganicheskaya Khimiya*, vol. 22, No. 2, pp. 149–152, (1996).

N. Beloglazova et al., "Site–specific Cleavage of Yeast tRNA(Phe) by Derivatives of Oligonucleotides Bearing Bismidazole Groups", *Doklady Akademii Nauk* (*Russia*), vol. 369, No. 6, pp. 827–830, (1999).

* cited by examiner

SEQUENCE LISTING

```
<160> NUMBER OF SEQ ID NOS: 91

<210> SEQ ID NO 1
<211> LENGTH: 21
<212> TYPE: DNA
<213> ORGANISM: Artificial Sequence
<220> FEATURE:
<223> OTHER INFORMATION: Oligonucleotide

<400> SEQUENCE: 1
gtaatacgac tcactatagg g                                              21

<210> SEQ ID NO 2
<211> LENGTH: 21
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (11)..(11)
<223> OTHER INFORMATION: 2'-succinimido-2'-deoxyuridine

<400> SEQUENCE: 2
gtaatacgac ncactatagg g                                              21

<210> SEQ ID NO 3
<211> LENGTH: 21
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (2)..(2)
<223> OTHER INFORMATION: 2'-succinimido-2'-deoxyuridine

<400> SEQUENCE: 3
gnaatacgac tcactatagg g                                              21

<210> SEQ ID NO 4
<211> LENGTH: 21
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (2)..(2)
<223> OTHER INFORMATION: 2'-succinimido-2'-deoxyuridine
<221> NAME/KEY: modified_base
<222> LOCATION: (5)..(5)
<223> OTHER INFORMATION: 2'-succinimido-2'-deoxyuridine
```

```
<221> NAME/KEY: modified_base
<222> LOCATION: (11)..(11)
<223> OTHER INFORMATION: 2'-succinimido-2'-deoxyuridine
<221> NAME/KEY: modified_base
<222> LOCATION: (15)..(15)
<223> OTHER INFORMATION: 2'-succinimido-2'-deoxyuridine
<221> NAME/KEY: modified_base
<222> LOCATION: (17)..(17)
<223> OTHER INFORMATION: 2'-succinimido-2'-deoxyuridine

<400> SEQUENCE: 4 gnaaacgac ncacnanagg g                                               21

<210> SEQ ID NO 5
<211> LENGTH: 21
<212> TYPE: DNA
<213> ORGANISM: Artificial Sequence
<220> FEATURE:
<223> OTHER INFORMATION: Oligonucleotide

<400> SEQUENCE: 5
ccctatagtg agtcgtatta c                                              21

<210> SEQ ID NO 6
<211> LENGTH: 21
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (19)..(19)
<223> OTHER INFORMATION: 2'-succinimido-2'-deoxyuridine

<400> SEQUENCE: 6
ccctatagtg agtcgtatna c                                              21

<210> SEQ ID NO 7
<211> LENGTH: 40
<212> TYPE: DNA
<213> ORGANISM: Artificial Sequence
<220> FEATURE:
<223> OTHER INFORMATION: Oligonucleotide

<400> SEQUENCE: 7
aaacgacggc cagtgaattg taatacgact cactataggg                          40

<210> SEQ ID NO 8
<211> LENGTH: 40
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (30)..(30)
<223> OTHER INFORMATION: 2'-succinimido-2'-deoxyuridine

<400> SEQUENCE: 8
aaacgacggc cagtgaattg taatacgacn cactataggg                          40

<210> SEQ ID NO 9
<211> LENGTH: 40
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (24)..(24)
<223> OTHER INFORMATION: 2'-succinimido-2'-deoxyuridine
<221> NAME/KEY: modified_base
```

```
<222> LOCATION: (30)..(30)
<223> OTHER INFORMATION: 2'-succinimido-2'-deoxyuridine
<221> NAME/KEY: modified_base
<222> LOCATION: (36)..(36)
<223> OTHER INFORMATION: 2'-succinimido-2'-deoxyuridine

<400> SEQUENCE: 9
aaacgacggc cagtgaattg taanacgacn cactanaggg                              40

<210> SEQ ID NO 10
<211> LENGTH: 40
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (14)..(14)
<223> OTHER INFORMATION: 2'-succinimido-2'-deoxyuridine
<221> NAME/KEY: modified_base
<222> LOCATION: (21)..(21)
<223> OTHER INFORMATION: 2'-succinimido-2'-deoxyuridine
<221> NAME/KEY: modified_base
<222> LOCATION: (24)..(24)
<223> OTHER INFORMATION: 2'-succinimido-2'-deoxyuridine
<221> NAME/KEY: modified_base
<222> LOCATION: (30)..(30)
<223> OTHER INFORMATION: 2'-succinimido-2'-deoxyuridine
<221> NAME/KEY: modified_base
<222> LOCATION: (34)..(34)
<223> OTHER INFORMATION: 2'-succinimido-2'-deoxyuridine
<221> NAME/KEY: modified_base
<222> LOCATION: (36)..(36)
<223> OTHER INFORMATION: 2'-succinimido-2'-deoxyuridine

<400> SEQUENCE: 10
aaacgacggc cagngaattg naanacgacn cacnanaggg                              40

<210> SEQ ID NO 11
<211> LENGTH: 52
<212> TYPE: DNA
<213> ORGANISM: Artificial Sequence
<220> FEATURE:
<223> OTHER INFORMATION: Oligonucleotide

<400> SEQUENCE: 11
cccccaaaaa ccctatagtg agtcgtatta caattcactg gccgtcgttt tt               52

<210> SEQ ID NO 12
<211> LENGTH: 52
<212> TYPE: DNA
<213> ORGANISM: Artificial Sequence
<220> FEATURE:
<223> OTHER INFORMATION: Oligonucleotide

<400> SEQUENCE: 12 aaaaccccc ccctatagtg agtcgtatta cttttttttt tttttttttt tt                52

<210> SEQ ID NO 13
<211> LENGTH: 31
<212> TYPE: DNA
<213> ORGANISM: Artificial Sequence
<220> FEATURE:
<223> OTHER INFORMATION: Oligonucleotide

<400> SEQUENCE: 13
ggctagctcc ctgccagcag ccgcggtaat a                                       31

<210> SEQ ID NO 14
<211> LENGTH: 31
```

```
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (27)..(27)
<223> OTHER INFORMATION: 2'-succinimido-2'-deoxyuridine

<400> SEQUENCE: 14
ggctagctcc ctgccagcag ccgcggnaat a                              31

<210> SEQ ID NO 15
<211> LENGTH: 31
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (4)..(4)
<223> OTHER INFORMATION: 2'-succinimido-2'-deoxyuridine
<221> NAME/KEY: modified_base
<222> LOCATION: (27)..(27)
<223> OTHER INFORMATION: 2'-succinimido-2'-deoxyuridine

<400> SEQUENCE: 15
ggcnagctcc ctgccagcag ccgcggnaat a                              31

<210> SEQ ID NO 16
<211> LENGTH: 31
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (4)..(4)
<223> OTHER INFORMATION: 2'-succinimido-2'-deoxyuridine
<221> NAME/KEY: modified_base
<222> LOCATION: (8)..(8)
<223> OTHER INFORMATION: 2'-succinimido-2'-deoxyuridine
<221> NAME/KEY: modified_base
<222> LOCATION: (12)..(12)
<223> OTHER INFORMATION: 2'-succinimido-2'-deoxyuridine
<221> NAME/KEY: modified_base
<222> LOCATION: (27)..(27)
<223> OTHER INFORMATION: 2'-succinimido-2'-deoxyuridine

<400> SEQUENCE: 16
ggcnagcncc cngccagcag ccgcggnaat a                              31

<210> SEQ ID NO 17
<211> LENGTH: 31
<212> TYPE: DNA
<213> ORGANISM: Artificial Sequence
<220> FEATURE:
<223> OTHER INFORMATION: Oligonucleotide

<400> SEQUENCE: 17
tattaccgcg gctgctggca gggagctagc c                              31

<210> SEQ ID NO 18
<211> LENGTH: 31
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (4)..(4)
<223> OTHER INFORMATION: 2'-succinimido-2'-deoxyuridine
<221> NAME/KEY: modified_base
<222> LOCATION: (13)..(13)
<223> OTHER INFORMATION: 2'-succinimido-2'-deoxyuridine
```

```
<221> NAME/KEY: modified_base
<222> LOCATION: (16)..(16)
<223> OTHER INFORMATION: 2'-succinimido-2'-deoxyuridine
<221> NAME/KEY: modified_base
<222> LOCATION: (27)..(27)
<223> OTHER INFORMATION: 2'-succinimido-2'-deoxyuridine

<400> SEQUENCE: 18
tatnaccgcg gcngcnggca gggagcnagc c                               31

<210> SEQ ID NO 19
<211> LENGTH: 10
<212> TYPE: DNA
<213> ORGANISM: Artificial Sequence
<220> FEATURE:
<223> OTHER INFORMATION: Oligonucleotide

<400> SEQUENCE: 19
tttttttttt                                                       10

<210> SEQ ID NO 20
<211> LENGTH: 10
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (9)..(9)
<223> OTHER INFORMATION: 2'-succinimido-2'-deoxyuridine

<400> SEQUENCE: 20 ttttttttnt                                                       10

<210> SEQ ID NO 21
<211> LENGTH: 10
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (8)..(8)
<223> OTHER INFORMATION: 2'-succinimido-2'-deoxyuridine

<400> SEQUENCE: 21 tttttttntt                                                       10

<210> SEQ ID NO 22
<211> LENGTH: 10
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (7)..(7)
<223> OTHER INFORMATION: 2'-succinimido-2'-deoxyuridine

<400> SEQUENCE: 22 ttttttnttt                                                       10

<210> SEQ ID NO 23
<211> LENGTH: 10
<212> TYPE: DNA
<213> ORGANISM: Artificial Sequence
<220> FEATURE:
<223> OTHER INFORMATION: Modified oligonucleotides
<221> NAME/KEY: modified_base
<222> LOCATION: (6)..(6)
<223> OTHER INFORMATION: 2'-succinimido-2'-deoxyuridine
```

```
<400> SEQUENCE: 23 tttttntttt                                                            10

<210> SEQ ID NO 24
<211> LENGTH: 10
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (3)..(3)
<223> OTHER INFORMATION: 2'-succinimido-2'-deoxyuridine

<400> SEQUENCE: 24 ttnttttttt                                                            10

<210> SEQ ID NO 25
<211> LENGTH: 10
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (2)..(2)
<223> OTHER INFORMATION: 2'-succinimido-2'-deoxyuridine

<400> SEQUENCE: 25 tntttttttt                                                            10

<210> SEQ ID NO 26
<211> LENGTH: 10
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (1)..(1)
<223> OTHER INFORMATION: 2'-succinimido-2'-deoxyuridine

<400> SEQUENCE: 26 nttttttttt                                                            10

<210> SEQ ID NO 27
<211> LENGTH: 21
<212> TYPE: DNA
<213> ORGANISM: Artificial Sequence
<220> FEATURE:
<223> OTHER INFORMATION: Oligonucleotide

<400> SEQUENCE: 27
attgtaatac gactcactat a                                               21

<210> SEQ ID NO 28
<211> LENGTH: 21
<212> TYPE: DNA
<213> ORGANISM: Artificial Sequence
<220> FEATURE:
<223> OTHER INFORMATION: Oligonucleotide

<400> SEQUENCE: 28
ttgtaatacg actcactata g                                               21

<210> SEQ ID NO 29
<211> LENGTH: 21
<212> TYPE: DNA
<213> ORGANISM: Artificial Sequence
<220> FEATURE:
```

```
<223> OTHER INFORMATION: Oligonucleotide

<400> SEQUENCE: 29
tgtaatacga ctcactatag g                                              21

<210> SEQ ID NO 30
<211> LENGTH: 28
<212> TYPE: DNA
<213> ORGANISM: Artificial Sequence
<220> FEATURE:
<223> OTHER INFORMATION: Oligonucleotide

<400> SEQUENCE: 30
cttttcgccc tatagtgagt cgtattac                                       28

<210> SEQ ID NO 31
<211> LENGTH: 28
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (4)..(4)
<223> OTHER INFORMATION: 2'-succinimido-2'-deoxyuridine

<400> SEQUENCE: 31
cttntcgccc tatagtgagt cgtattac                                       28

<210> SEQ ID NO 32
<211> LENGTH: 28
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (2)..(2)
<223> OTHER INFORMATION: 2'-succinimido-2'-deoxyuridine
<221> NAME/KEY: modified_base
<222> LOCATION: (3)..(3)
<223> OTHER INFORMATION: 2'-succinimido-2'-deoxyuridine
<221> NAME/KEY: modified_base
<222> LOCATION: (4)..(4)
<223> OTHER INFORMATION: 2'-succinimido-2'-deoxyuridine

<400> SEQUENCE: 32
cnnntcgccc tatagtgagt cgtattac                                       28

<210> SEQ ID NO 33
<211> LENGTH: 28
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (11)..(11)
<223> OTHER INFORMATION: 2'-succinimido-2'-deoxyuridine

<400> SEQUENCE: 33
cttttcgccc natagtgagt cgtattac                                       28

<210> SEQ ID NO 34
<211> LENGTH: 21
<212> TYPE: DNA
<213> ORGANISM: Artificial Sequence
<220> FEATURE:
<223> OTHER INFORMATION: Oligonucleotide
<221> NAME/KEY: modified_base
<222> LOCATION: (19)..(19)
<223> OTHER INFORMATION: 2'-succinimido-2'-deoxyuridine
```

```
<400> SEQUENCE: 34
ttgtaatacg actcactana g                                              21

<210> SEQ ID NO 35
<211> LENGTH: 21
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (18)..(18)
<223> OTHER INFORMATION: 2'-succinimido-2'-deoxyuridine

<400> SEQUENCE: 35
tgtaatacga ctcactanag g                                              21

<210> SEQ ID NO 36
<211> LENGTH: 21
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (17)..(17)
<223> OTHER INFORMATION: 2'-succinimido-2'-deoxyuridine

<400> SEQUENCE: 36
gtaatacgac tcactanagg g                                              21

<210> SEQ ID NO 37
<211> LENGTH: 21
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (16)..(16)
<223> OTHER INFORMATION: 2'-succinimido-2'-deoxyuridine

<400> SEQUENCE: 37
tgtaatacga ctcacnatag g                                              21

<210> SEQ ID NO 38
<211> LENGTH: 21
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (15)..(15)
<223> OTHER INFORMATION: 2'-succinimido-2'-deoxyuridine

<400> SEQUENCE: 38
gtaatacgac tcacnatagg g                                              21

<210> SEQ ID NO 39
<211> LENGTH: 21
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (14)..(14)
<223> OTHER INFORMATION: 2'-succinimido-2'-deoxyuridine

<400> SEQUENCE: 39
atacgactca ctanagggcg a                                              21
```

<210> SEQ ID NO 40
<211> LENGTH: 21
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (13)..(13)
<223> OTHER INFORMATION: 2'-succinimido-2'-deoxyuridine

<400> SEQUENCE: 40
ttgtaatacg acncactata g                                          21

<210> SEQ ID NO 41
<211> LENGTH: 21
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (12)..(12)
<223> OTHER INFORMATION: 2'-succinimido-2'-deoxyuridine

<400> SEQUENCE: 41
tgtaatacga cncactatag g                                          21

<210> SEQ ID NO 42
<211> LENGTH: 21
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (2)..(2)
<223> OTHER INFORMATION: 2'-succinimido-2'-deoxyuridine

<400> SEQUENCE: 42
gnaatacgac tcactatagg g                                          21

<210> SEQ ID NO 43
<211> LENGTH: 18
<212> TYPE: DNA
<213> ORGANISM: Artificial Sequence
<220> FEATURE:
<223> OTHER INFORMATION: Oligonucleotide

<400> SEQUENCE: 43
tgtaaaacga cggccagt                                              18

<210> SEQ ID NO 44
<211> LENGTH: 18
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (15)..(15)
<223> OTHER INFORMATION: 2'-methoxyoxalamido-2'-deoxycytidine

<400> SEQUENCE: 44
tgtaaaacga cggcnagt                                              18

<210> SEQ ID NO 45
<211> LENGTH: 18
<212> TYPE: DNA
<213> ORGANISM: Artificial Sequence
<220> FEATURE:

```
<223> OTHER INFORMATION: Modified oligonucleotide
<221> NAME/KEY: modified_base
<222> LOCATION: (14)..(14)
<223> OTHER INFORMATION: 2'-methoxyoxalamido-2'-deoxycytidine

<400> SEQUENCE: 45
tgtaaaacga cggncagt                                                        18

<210> SEQ ID NO 46
<211> LENGTH: 18
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (11)..(11)
<223> OTHER INFORMATION: 2'-methoxyoxalamido-2'-deoxycytidine

<400> SEQUENCE: 46
tgtaaaacga nggccagt                                                        18

<210> SEQ ID NO 47
<211> LENGTH: 18
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (8)..(8)
<223> OTHER INFORMATION: 2'-methoxyoxalamido-2'-deoxycytidine

<400> SEQUENCE: 47
tgtaaaanga cggccagt                                                        18

<210> SEQ ID NO 48
<211> LENGTH: 18
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (8)..(8)
<223> OTHER INFORMATION: 2'-methoxyoxalamido-2'deoxycytidine
<221> NAME/KEY: modified_base
<222> LOCATION: (14)..(14)
<223> OTHER INFORMATION: 2'-methoxyoxalamido-2'deoxycytidine

<400> SEQUENCE: 48
tgtaaaanga cggncagt                                                        18

<210> SEQ ID NO 49
<211> LENGTH: 18
<212> TYPE: DNA
<213> ORGANISM: Artificial Sequence
<220> FEATURE:
<223> OTHER INFORMATION: Oligonucleotide

<400> SEQUENCE: 49
caggaaacag ctatgacc                                                        18

<210> SEQ ID NO 50
<211> LENGTH: 18
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (17)..(17)
<223> OTHER INFORMATION: 2'-methoxyoxalamido-2'-deoxycytidine
```

```
<400> SEQUENCE: 50
caggaaacag ctatganc                                                 18

<210> SEQ ID NO 51
<211> LENGTH: 18
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (11)..(11)
<223> OTHER INFORMATION: 2'-methoxyoxalamido-2'-deoxycytidine

<400> SEQUENCE: 51
caggaaacag ntatgacc                                                 18

<210> SEQ ID NO 52
<211> LENGTH: 35
<212> TYPE: DNA
<213> ORGANISM: Artificial Sequence
<220> FEATURE:
<223> OTHER INFORMATION: Oligonucleotide

<400> SEQUENCE: 52
acggccagtg aattgtaata cgactcacta taggg                              35

<210> SEQ ID NO 53
<211> LENGTH: 35
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (31)..(31)
<223> OTHER INFORMATION: 2'-succinimido-2'-deoxyuridine

<400> SEQUENCE: 53
acggccagtg aattgtaata cgactcacta naggg                              35

<210> SEQ ID NO 54
<211> LENGTH: 18
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (1)..(1)
<223> OTHER INFORMATION: 2'-succinimido-2'-deoxyuridine

<400> SEQUENCE: 54
ngtaaaacga cggccagt                                                 18

<210> SEQ ID NO 55
<211> LENGTH: 19
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (1)..(1)
<223> OTHER INFORMATION: 2'-succinimido-2'-deoxyuridine

<400> SEQUENCE: 55
ncaggaaaca gctatgacc                                                19

<210> SEQ ID NO 56
```

```
<211> LENGTH: 22
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (1)..(1)
<223> OTHER INFORMATION: 2'-succinimido-2'-deoxyuridine

<400> SEQUENCE: 56
ncgccaagct atttaggtga ca                                               22

<210> SEQ ID NO 57
<211> LENGTH: 35
<212> TYPE: DNA
<213> ORGANISM: Artificial Sequence
<220> FEATURE:
<223> OTHER INFORMATION: Oligonucleotide

<400> SEQUENCE: 57
acggccagtg aattgtaata cgactcacta taggg                                 35

<210> SEQ ID NO 58
<211> LENGTH: 35
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (31)..(31)
<223> OTHER INFORMATION: 2'-methylamidooxalamido-2'-deoxyuridine

<400> SEQUENCE: 58
acggccagtg aattgtaata cgactcacta naggg                                 35

<210> SEQ ID NO 59
<211> LENGTH: 32
<212> TYPE: DNA
<213> ORGANISM: Artificial Sequence
<220> FEATURE:
<223> OTHER INFORMATION: Oligonucleotide

<400> SEQUENCE: 59
ggtagcgact catgagtaaa ccgttcaaac tg                                    32

<210> SEQ ID NO 60
<211> LENGTH: 32
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (25)..(25)
<223> OTHER INFORMATION: 2'-succinimido-2'-deoxyuridine

<400> SEQUENCE: 60
ggtagcgact catgagtaaa ccgtncaaac tg                                    32

<210> SEQ ID NO 61
<211> LENGTH: 32
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (28)..(28)
<223> OTHER INFORMATION: 2'-methoxyoxalamido-2'-deoxyuridine

<400> SEQUENCE: 61
```
gtcacgtcag tagtacggaa gtagaacngc gg                                32

<210> SEQ ID NO 62
<211> LENGTH: 38
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (13)..(13)
<223> OTHER INFORMATION: 2'-succinimido-2'-deoxyuridine
<221> NAME/KEY: modified_base
<222> LOCATION: (34)..(34)
<223> OTHER INFORMATION: 2'-succinimido-2'-deoxyuridine

<400> SEQUENCE: 62
tgacgggcgg tgngtgcaag gcccggggac gtantcac                          38

<210> SEQ ID NO 63
<211> LENGTH: 26
<212> TYPE: DNA
<213> ORGANISM: Artificial Sequence
<220> FEATURE:
<223> OTHER INFORMATION: Oligonucleotide

<400> SEQUENCE: 63
gatttcgcgg gtggcaccgt ggtgca                                       26

<210> SEQ ID NO 64
<211> LENGTH: 26
<212> TYPE: DNA
<213> ORGANISM: Artificial Sequence
<220> FEATURE:
<223> OTHER INFORMATION: Degenerate oligonucleotide
<221> NAME/KEY: misc_feature
<222> LOCATION: (15)..(15)
<223> OTHER INFORMATION: a or t or g or c
<221> NAME/KEY: misc_feature
<222> LOCATION: (18)..(18)
<223> OTHER INFORMATION: a or t or g or c
<221> NAME/KEY: misc_feature
<222> LOCATION: (24)..(24)
<223> OTHER INFORMATION: a or t or g or c

<400> SEQUENCE: 64
gatttygcgg gtggnacngt ggtnca                                       26

<210> SEQ ID NO 65
<211> LENGTH: 26
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (12)..(12)
<223> OTHER INFORMATION: 2'-succinimido-2'-deoxyuridine
<221> NAME/KEY: misc_feature
<222> LOCATION: (15)..(15)
<223> OTHER INFORMATION: a or t or g or c
<221> NAME/KEY: misc_feature
<222> LOCATION: (18)..(18)
<223> OTHER INFORMATION: a or t or g or c
<221> NAME/KEY: misc_feature
<222> LOCATION: (24)..(24)
<223> OTHER INFORMATION: a or t or g or c

<400> SEQUENCE: 65
gatttygcgg gnggnacngt ggtnca                                       26

```
<210> SEQ ID NO 66
<211> LENGTH: 26
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (12)..(12)
<223> OTHER INFORMATION: 2'-succinimido-2'-deoxyuridine
<221> NAME/KEY: misc_feature
<222> LOCATION: (15)..(15)
<223> OTHER INFORMATION: a or t or g or c
<221> NAME/KEY: misc_feature
<222> LOCATION: (18)..(18)
<223> OTHER INFORMATION: a or t or g or c
<221> NAME/KEY: modified_base
<222> LOCATION: (20)..(20)
<223> OTHER INFORMATION: 2'-succinimido-2'-deoxyuridine
<221> NAME/KEY: misc_feature
<222> LOCATION: (24)..(24)
<223> OTHER INFORMATION: a or t or g or c

<400> SEQUENCE: 66
gatttygcgg gnggnacngn ggtnca                                    26

<210> SEQ ID NO 67
<211> LENGTH: 24
<212> TYPE: DNA
<213> ORGANISM: Artificial Sequence
<220> FEATURE:
<223> OTHER INFORMATION: Oligonucleotide

<400> SEQUENCE: 67
caaaaaaaaa acactttttt tttt                                      24

<210> SEQ ID NO 68
<211> LENGTH: 21
<212> TYPE: DNA
<213> ORGANISM: Artificial Sequence
<220> FEATURE:
<223> OTHER INFORMATION: Oligonucleotide

<400> SEQUENCE: 68
actgagactc taatcgatta g                                         21

<210> SEQ ID NO 69
<211> LENGTH: 25
<212> TYPE: DNA
<213> ORGANISM: Artificial Sequence
<220> FEATURE:
<223> OTHER INFORMATION: Oligonucleotide

<400> SEQUENCE: 69
caaaaaaaaa acactttttt ttttg                                     25

<210> SEQ ID NO 70
<211> LENGTH: 22
<212> TYPE: DNA
<213> ORGANISM: Artificial Sequence
<220> FEATURE:
<223> OTHER INFORMATION: Oligonucleotide

<400> SEQUENCE: 70
actgagactc taatcgatta ga                                        22

<210> SEQ ID NO 71
<211> LENGTH: 10
<212> TYPE: DNA
<213> ORGANISM: Artificial Sequence
```

```
<220> FEATURE:
<223> OTHER INFORMATION: Oligonucleotide

<400> SEQUENCE: 71
tttttggggg                                                              10

<210> SEQ ID NO 72
<211> LENGTH: 10
<212> TYPE: DNA
<213> ORGANISM: Artificial Sequence
<220> FEATURE:
<223> OTHER INFORMATION: Oligonucleotide

<400> SEQUENCE: 72
gggggttttt                                                              10

<210> SEQ ID NO 73
<211> LENGTH: 40
<212> TYPE: DNA
<213> ORGANISM: Homo sapiens

<400> SEQUENCE: 73
caagcttgtt ttaaaccatt aggtttaagg gtgttttta                               40

<210> SEQ ID NO 74
<211> LENGTH: 40
<212> TYPE: DNA
<213> ORGANISM: Homo sapiens

<400> SEQUENCE: 74
aagcttcggg aaccatgtct ttaggtaagt gaggcaacag                              40

<210> SEQ ID NO 75
<211> LENGTH: 69
<212> TYPE: DNA
<213> ORGANISM: Escherichia coli
<220> FEATURE:
<221> NAME/KEY: misc_feature
<222> LOCATION: (20)..(20)
<223> OTHER INFORMATION: a or g or c or t/u, unknown, or other
<221> NAME/KEY: misc_feature
<222> LOCATION: (29)..(29)
<223> OTHER INFORMATION: a or g or c or t/u, unknown, or other
<221> NAME/KEY: misc_feature
<222> LOCATION: (41)..(41)
<223> OTHER INFORMATION: a or g or c or t/u, unknown, or other

<400> SEQUENCE: 75
tcgaagaggg gctggaagan ggcctggcnc accacacctt ncttggggtg actggtcatg        60
gaaaacctt                                                               69

<210> SEQ ID NO 76
<211> LENGTH: 70
<212> TYPE: DNA
<213> ORGANISM: Escherichia coli

<400> SEQUENCE: 76
tcgaagaggg gctggaagat ggcctggcgc accagacgtt acttggcgtg actggctcag        60
ggaaaacctt                                                              70

<210> SEQ ID NO 77
<211> LENGTH: 146
<212> TYPE: DNA
<213> ORGANISM: Artificial Sequence
<220> FEATURE:
```

```
<223> OTHER INFORMATION: pGEM-3zfp
<221> NAME/KEY: misc_feature
<222> LOCATION: (58)..(58)
<223> OTHER INFORMATION: a or g or c or t/u, unknown, or other
<221> NAME/KEY: misc_feature
<222> LOCATION: (79)..(79)
<223> OTHER INFORMATION: a or g or c or t/u, unknown, or other
<221> NAME/KEY: misc_feature
<222> LOCATION: (85)..(85)
<223> OTHER INFORMATION: a or g or c or t/u, unknown, or other
<221> NAME/KEY: misc_feature
<222> LOCATION: (101)..(101)
<223> OTHER INFORMATION: a or g or c or t/u, unknown, or other
<221> NAME/KEY: misc_feature
<222> LOCATION: (132)..(132)
<223> OTHER INFORMATION: a or g or c or t/u, unknown, or other

<400> SEQUENCE: 77
tcggaacccg gggatcctct agagttcgac ctgcaggcat gcaagcttga gtattctnta     60
gtgttcacct aaatagcttg gcngtaatna tggtcatagc tgttncctgt gtgaaattgg    120
tatccgctca caatancaca caacat                                         146

<210> SEQ ID NO 78
<211> LENGTH: 143
<212> TYPE: DNA
<213> ORGANISM: Artificial Sequence
<220> FEATURE:
<223> OTHER INFORMATION: pGEM-3zfp

<400> SEQUENCE: 78
tcggtacccg gggatcctct agagtcgacc tgcaggcatg caagcttgag tattctatag     60
tgtcacctaa atagcttggc gtaatcatgg tcatagctgt tcctgtgtg aaattgttat    120 ccgctcacaa ttccacacaa cat                                            143

<210> SEQ ID NO 79
<211> LENGTH: 145
<212> TYPE: DNA
<213> ORGANISM: Escherichia coli
<220> FEATURE:
<221> NAME/KEY: misc_feature
<222> LOCATION: (110)..(110)
<223> OTHER INFORMATION: a or g or c or t/u, unknown, or other

<400> SEQUENCE: 79
tactagcatt ccgacttcat ggagtcgagt tgcgactcca atccgactac accactaaga     60
ggccgctgct ctcgcaggtc gttctcttgt atgcgccatt gaacacgtgn gacccgccaa    120
aggccatgat gactagacgc atccc                                          145

<210> SEQ ID NO 80
<211> LENGTH: 165
<212> TYPE: DNA
<213> ORGANISM: Escherichia coli

<400> SEQUENCE: 80
ccctactgca gttcagtagt accgggaatg ctggtcccga tgtgtgcacg atgttaccgc     60
gtatgtttct cttcgctgga gcgctctcgt tcgcctggag tatttcacgc agcatcaggc    120
ctaacctcag acgttgagct gaggtacttc agccttagcg atcat                    165

<210> SEQ ID NO 81
<211> LENGTH: 22
<212> TYPE: DNA
<213> ORGANISM: Artificial Sequence
<220> FEATURE:
```

<223> OTHER INFORMATION: Oligonucleotide

<400> SEQUENCE: 81
ccacggtgcc acccgcgaaa tc                                              22

<210> SEQ ID NO 82
<211> LENGTH: 48
<212> TYPE: DNA
<213> ORGANISM: Artificial Sequence
<220> FEATURE:
<223> OTHER INFORMATION: Oligonucleotide

<400> SEQUENCE: 82
gatttcgcgg gtggcaccgt ggtgcaccac ggtgccaccc gcgaaatc                  48

<210> SEQ ID NO 83
<211> LENGTH: 26
<212> TYPE: DNA
<213> ORGANISM: Artificial Sequence
<220> FEATURE:
<223> OTHER INFORMATION: Oligonucleotide
<221> NAME/KEY: misc_feature
<222> LOCATION: (3)..(3)
<223> OTHER INFORMATION: a or g or c or t/u, unknown, or other
<221> NAME/KEY: misc_feature
<222> LOCATION: (9)..(9)
<223> OTHER INFORMATION: a or g or c or t/u, unknown, or other
<221> NAME/KEY: misc_feature
<222> LOCATION: (12)..(12)
<223> OTHER INFORMATION: a or g or c or t/u, unknown, or other
<221> NAME/KEY: misc_feature
<222> LOCATION: (21)..(21)
<223> OTHER INFORMATION: a or g or c or t/u, unknown, or other

<400> SEQUENCE: 83
acntggtgnc anggtgggcg ntttag                                          26

<210> SEQ ID NO 84
<211> LENGTH: 48
<212> TYPE: DNA
<213> ORGANISM: Artificial Sequence
<220> FEATURE:
<223> OTHER INFORMATION: Oligonucleotide
<221> NAME/KEY: misc_feature
<222> LOCATION: (15)..(15)
<223> OTHER INFORMATION: a or g or c or t/u, unknown, or other
<221> NAME/KEY: misc_feature
<222> LOCATION: (18)..(18)
<223> OTHER INFORMATION: a or g or c or t/u, unknown, or other
<221> NAME/KEY: misc_feature
<222> LOCATION: (24)..(24)
<223> OTHER INFORMATION: a or g or c or t/u, unknown, or other
<221> NAME/KEY: misc_feature
<222> LOCATION: (31)..(31)
<223> OTHER INFORMATION: a or g or c or t/u, unknown, or other
<221> NAME/KEY: misc_feature
<222> LOCATION: (35)..(35)
<223> OTHER INFORMATION: a or g or c or t/u, unknown, or other

<400> SEQUENCE: 84
gatttygcgg gtggnacngt ggtncaccac ngtcncaccc gcraaatc                  48

<210> SEQ ID NO 85
<211> LENGTH: 48
<212> TYPE: DNA
<213> ORGANISM: Artificial Sequence
<220> FEATURE:
<223> OTHER INFORMATION: Oligonucleotide
<221> NAME/KEY: misc_feature
<222> LOCATION: (15)..(15)
<223> OTHER INFORMATION: a or g or c or t/u, unknown, or other

```
<221> NAME/KEY: misc_feature
<222> LOCATION: (18)..(18)
<223> OTHER INFORMATION: a or g or c or t/u, unknown, or other
<221> NAME/KEY: misc_feature
<222> LOCATION: (24)..(24)
<223> OTHER INFORMATION: a or g or c or t/u, unknown, or other
<221> NAME/KEY: misc_feature
<222> LOCATION: (31)..(31)
<223> OTHER INFORMATION: a or g or c or t/u, unknown, or other
<221> NAME/KEY: misc_feature
<222> LOCATION: (34)..(34)
<223> OTHER INFORMATION: a or g or c or t/u, unknown, or other

<400> SEQUENCE: 85
gatttygcgg gtggnacngt ggtncaccac ngtnccaccc gcraaatc        48

<210> SEQ ID NO 86
<211> LENGTH: 26
<212> TYPE: DNA
<213> ORGANISM: Artificial Sequence
<220> FEATURE:
<223> OTHER INFORMATION: Modified oligonucleotide
<221> NAME/KEY: misc_feature
<222> LOCATION: (6)..(6)
<223> OTHER INFORMATION: a or g or c or t/u, unknown, or other
<221> NAME/KEY: modified_base
<222> LOCATION: (12)..(12)
<223> OTHER INFORMATION: 2'-succinimido-2'-deoxyuridine
<221> NAME/KEY: misc_feature
<222> LOCATION: (15)..(15)
<223> OTHER INFORMATION: a or g or c or t/u, unknown, or other
<221> NAME/KEY: misc_feature
<222> LOCATION: (18)..(18)
<223> OTHER INFORMATION: a or g or c or t/u, unknown, or other
<221> NAME/KEY: misc_feature
<222> LOCATION: (24)..(24)
<223> OTHER INFORMATION: a or g or c or t/u, unknown, or other

<400> SEQUENCE: 86
gatttngcgg gnggnacngt ggtnca        26

<210> SEQ ID NO 87
<211> LENGTH: 36
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (12)..(12)
<223> OTHER INFORMATION: 2'-succinimido-2'-deoxyuridine
<221> NAME/KEY: misc_feature
<222> LOCATION: (14)..(14)
<223> OTHER INFORMATION: a or g or c or t/u, unknown, or other
<221> NAME/KEY: misc_feature
<222> LOCATION: (18)..(18)
<223> OTHER INFORMATION: a or g or c or t/u, unknown, or other
<221> NAME/KEY: misc_feature
<222> LOCATION: (24)..(24)
<223> OTHER INFORMATION: a or g or c or t/u, unknown, or other
<221> NAME/KEY: misc_feature
<222> LOCATION: (31)..(31)
<223> OTHER INFORMATION: a or g or c or t/u, unknown, or other
<221> NAME/KEY: misc_feature
<222> LOCATION: (34)..(34)
<223> OTHER INFORMATION: a or g or c or t/u, unknown, or other

<400> SEQUENCE: 87
gatttygcgg gngncacngt ggtncaccac ngtncc        36

<210> SEQ ID NO 88
<211> LENGTH: 36
<212> TYPE: DNA
<213> ORGANISM: Artificial Sequence
```

```
<220> FEATURE:
<223> OTHER INFORMATION: Modified oligonucleotide
<221> NAME/KEY: misc_feature
<222> LOCATION: (6)..(6)
<223> OTHER INFORMATION: a or g or c or t/u, unknown, or other
<221> NAME/KEY: modified_base
<222> LOCATION: (12)..(12)
<223> OTHER INFORMATION: 2'-succinimido-2'-deoxyuridine
<221> NAME/KEY: misc_feature
<222> LOCATION: (15)..(15)
<223> OTHER INFORMATION: a or g or c or t/u, unknown, or other
<221> NAME/KEY: misc_feature
<222> LOCATION: (18)..(18)
<223> OTHER INFORMATION: a or g or c or t/u, unknown, or other
<221> NAME/KEY: misc_feature
<222> LOCATION: (24)..(24)
<223> OTHER INFORMATION: a or g or c or t/u, unknown, or other
<221> NAME/KEY: misc_feature
<222> LOCATION: (31)..(31)
<223> OTHER INFORMATION: a or g or c or t/u, unknown, or other
<221> NAME/KEY: misc_feature
<222> LOCATION: (35)..(35)
<223> OTHER INFORMATION: a or g or c or t/u, unknown, or other

<400> SEQUENCE: 88
gatttngcgg gnggnacngt ggtncaccac ngtgnc                              36

<210> SEQ ID NO 89
<211> LENGTH: 26
<212> TYPE: DNA
<213> ORGANISM: Artificial Sequence
<220> FEATURE:
<223> OTHER INFORMATION: Modified oligonucleotide
<221> NAME/KEY: misc_feature
<222> LOCATION: (6)..(6)
<223> OTHER INFORMATION: a or g or c or t/u, unknown, or other
<221> NAME/KEY: modified_base
<222> LOCATION: (12)..(12)
<223> OTHER INFORMATION: 2'-succinimido-2'-deoxyuridine
<221> NAME/KEY: misc_feature
<222> LOCATION: (15)..(15)
<223> OTHER INFORMATION: a or g or c or t/u, unknown, or other
<221> NAME/KEY: misc_feature
<222> LOCATION: (18)..(18)
<223> OTHER INFORMATION: a or g or c or t/u, unknown, or other
<221> NAME/KEY: modified_base
<222> LOCATION: (20)..(20)
<223> OTHER INFORMATION: 2'-succinimido-2'-deoxyuridine
<221> NAME/KEY: misc_feature
<222> LOCATION: (24)..(24)
<223> OTHER INFORMATION: a or g or c or t/u, unknown, or other

<400> SEQUENCE: 89
gatttngcgg gnggnacngn ggtnca                                         26

<210> SEQ ID NO 90
<211> LENGTH: 28
<212> TYPE: DNA
<213> ORGANISM: Artificial Sequence
<220> FEATURE:
<223> OTHER INFORMATION: Modified oligonucleotide
<221> NAME/KEY: modified_base
<222> LOCATION: (12)..(12)
<223> OTHER INFORMATION: 2'-succinimido-2'-deoxyuridine
<221> NAME/KEY: misc_feature
<222> LOCATION: (15)..(15)
<223> OTHER INFORMATION: a or g or c or t/u, unknown, or other
<221> NAME/KEY: misc_feature
<222> LOCATION: (18)..(18)
<223> OTHER INFORMATION: a or g or c or t/u, unknown, or other
<221> NAME/KEY: modified_base
<222> LOCATION: (20)..(20)
<223> OTHER INFORMATION: 2'-succinimido-2'-deoxyuridine
<221> NAME/KEY: misc_feature
<222> LOCATION: (24)..(24)
```

-continued

```
<223> OTHER INFORMATION: a or g or c or t/u, unknown, or other

<400> SEQUENCE: 90
gatttygcgg gnggnacngn ggtncacc                                        28

<210> SEQ ID NO 91
<211> LENGTH: 28
<212> TYPE: DNA
<213> ORGANISM: Artificial Sequence
<220> FEATURE:
<223> OTHER INFORMATION: Modified oligonucleotide
<221> NAME/KEY: misc_feature
<222> LOCATION: (6)..(6)
<223> OTHER INFORMATION: a or g or c or t/u, unknown, or other
<221> NAME/KEY: modified_base
<222> LOCATION: (12)..(12)
<223> OTHER INFORMATION: 2'succinimido-2'-deoxyuridine
<221> NAME/KEY: misc_feature
<222> LOCATION: (15)..(15)
<223> OTHER INFORMATION: a or g or c or t/u, unknown, or other
<221> NAME/KEY: misc_feature
<222> LOCATION: (18)..(18)
<223> OTHER INFORMATION: a or g or c or t/u, unknown, or other
<221> NAME/KEY: modified_base
<222> LOCATION: (20)..(20)
<223> OTHER INFORMATION: 2'-succinimido-2'-deoxyuridine
<221> NAME/KEY: misc_feature
<222> LOCATION: (24)..(24)
<223> OTHER INFORMATION: a or g or c or t/u, unknown, or other

<400> SEQUENCE: 91
gatttngcgg gnggnacngn ggtncacc                                        28
```

INHIBITION OF MOLECULAR AND BIOLOGICAL PROCESSES USING MODIFIED OLIGONUCLEOTIDES

This invention was made with government support, including a grant, Grant No. DE-FG02-98ER82557, from the U.S. Department of Energy, and a grant, Grant No. R44-GM55485, from the U.S. National Institutes of Health. The U.S. government may have certain rights in the invention.

BACKGROUND OF THE INVENTION

Oligonucleotides are widely used in DNA technologies. One of the most important properties of an oligonucleotide is its ability to bind to a complementary sequence in other polynucleotides. Robust and specific annealing of an oligonucleotide to its complementary sequence is important for the success of probe hybridization methods that allow detection and quantification of pathogens, genomic mutations and other nucleotide sequences. Unfortunately, some oligonucleotides composed of the naturally occurring nucleotides cannot be used as robust probes. For example, an oligonucleotide containing two segments of sequences that are complementary to each other (e.g., CAAAAAAAAAACAC TTTTTTTTTT (SEQ ID NO: 67)) would form an internal structure called a hairpin that would prevent hybridization to its target. A further example is an oligonucleotide that can form a dimer with its second copy (e.g., ACTGAGACT CTAATCGATTAG (SEQ ID NO: 68)). Thus, there is a need for a method to inhibit the formation of such undesired structures.

Another typically unwanted biological or molecular process is the annealing of an oligonucleotide to non-target sequences in polynucleotides, called non-specific hybridization. This process increases the background signal in probe hybridization that limits the applications of this method and may lead to false positive results. The discrimination between specific and non-specific hybridization is most challenging when polynucleotides contain sequences that are similar to the target sequence. Another challenging situation is when very long polynucleotides (e.g., genomic DNA of 1 million (1 Mb) to 3 billion (3 Gb) base pairs) with a large amount of potential non-specific targets are present. Thus, there is a need for a method to inhibit non-specific hybridization of oligonucleotides.

There is a relatively narrow range of conditions (temperature, concentrations of ions and denaturing reagents) at which an oligonucleotide anneals specifically to its complementary target. These conditions are usually determined by measuring melting temperature ($T_m$) of a duplex comprising an oligonucleotide and the second oligonucleotide that contains a sequence of bases complementary to the first oligonucleotide. Unfortunately, the range of conditions for the specific annealing of an oligonucleotide may not coincide with other requirements of the intended method. A common practice to meet these requirements is to select the length and GC content of an oligonucleotide probe with appropriate melting temperature. This selection may contradict other requirements on the length of an oligonucleotide. For example, a 40-mer oligonucleotide that has only one complementary sequence in a genomic DNA sequence generally has too high of a melting temperature and would anneal to partially complementary targets while a 15-mer oligonucleotide that has a suitable melting temperature would have too many complementary sequences in a genomic DNA sequence. Thus, there is a need for a method to inhibit non-specific hybridization of oligonucleotides at the wide variety of stringency conditions dictated by the requirements, other than the melting temperature, of nucleotide sequences.

Oligonucleotides and complexes with other polynucleotides are widely used as substrates for protein binding and enzymatic reactions. The enzymatic reaction typically results in chemical modification of an oligonucleotide, including cleavage of the oligonucleotide or addition of extra nucleotide(s). The latter reaction may be catalyzed by polymerase that uses an oligonucleotide as a primer and adds bases complementary to the bases in the template polynucleotide. Polymerase may also use an oligonucleotide as a template for polymerization reaction. Enzymatic reactions involving oligonucleotides constitute the core of many DNA technologies, for example, PCR, DNA sequencing, and SNP detection. The formation of undesired structures by an oligonucleotide or its complexes with other polynucleotides may interfere with the intended enzymatic reaction. Moreover, even transient formation of such undesired structures in a minute fraction of oligonucleotides could be amplified by the enzymatic reaction. One example of such an undesired process is the non-specific amplification by PCR that is difficult to avoid if the number of amplification cycles exceeds 40. Another such example is primer-dimer amplification during PCR. Thus, there is a need for a method to inhibit the ability of oligonucleotides to form such undesired structures in enzymatic reactions.

Oligonucleotides may serve different functions in DNA technologies that involve enzymatic reactions. One example is as a probe for detection of specific sequences amplified by PCR with two primers in a TaqMan assay. Such a probe should specifically bind to its complementary sequence and potential polymerization of the probe should be inhibited. Thus, under such circumstances, there is a need for a method to inhibit non-specific hybridization of an oligonucleotide and to inhibit its ability to function as a primer.

Oligonucleotides are also used as primers in primer extension reactions for SNP detection, which comprises one or more cycles of adding, by action of DNA polymerase, a labeled nucleotide to a primer annealed to its target complementary sequence. The results of this method would be jeopardized if the primer extension occurs at sites of non-specific annealing of the primer or if the primer itself serves as a template. For example, a hairpin C AAAAAAAAAACACTTTTTTTTTT (SEQ ID NO: 67) and dimer of ACTGAGACTCTAATCGATTAG (SEQ ID NO: 68) oligonucleotides could serve as templates and the resulting undesired products will be C AAAAAAAAAACACTTTTTTTTTTg (SEQ ID NO: 69) and ACTGAGACTCTAATCGATTAGa (SEQ ID NO: 70).

Oligonucleotides are also used as primers in primer extension reactions for DNA sequencing, which comprises one or more cycles of adding nucleotides, by action of DNA polymerase, to a primer annealed to its target complementary sequence and terminating the extension reaction at a specific base encoded in the template. The undesired processes described in the previous paragraph would jeopardize the results of this method. Undesired primer extension products may have additional bases at their 3' ends and potentially could prime the reaction from targets that are complementary to the newly formed primers rather than to the original primers. In addition, polynucleotide products generated by the original primer extension could serve as templates for the annealing of the second copy of the primer and its subsequent extension. Should this event occur, it could generate a polynucleotide that has a primer sequence at its 5' end and a sequence complementary to the primer at its 3' end. DNA polymerase would generate the latter sequence at the final steps of the extension of the second copy of the primer when the nucleotides that comprise the first copy of the primer serve as templates. This polynucleotide would trigger exponential amplification (non-specific PCR) in a cycle sequencing method based on linear multiplication of products. Eventually, non-specific exponential amplification would overwhelm the linear multiplication and jeopardize the outcome of DNA sequencing. This undesired process limits the utility of such a cycle sequencing method. Thus, there is a need for a method to inhibit non-specific hybridization of an oligonucleotide, while retaining its ability to function as a primer and inhibiting its ability to function as a template in a polymerization reaction.

Oligonucleotides are also used as primers in primer extension reactions for PCR amplification, which comprises several cycles of adding nucleotides, by action of DNA polymerase, to primers annealed to target complementary sequences and termination of the extension reaction at the template end that is composed of nucleotides of another primer. The final 3' end nucleotide added by DNA polymerase is complementary to the 5' nucleotide of the other primer, and the final PCR product is the double stranded DNA with blunt ends. However, some polymerases (e.g., Taq polymerase) could add one more non-templated nucleotide (dA). The result would be a mixture of duplexes that differ in length by one nucleotide. This problem makes it difficult to interpret the results of PCR for genotyping. Thus, there is a need for a method to inhibit non-specific hybridization of an oligonucleotide, while retaining its ability to function as a primer for PCR amplification and allowing termination of polymerization reactions at a defined site on the primer when it serves as a template.

Oligonucleotides may serve different functions in DNA technologies. These differences often preclude the use of the same oligonucleotide in different applications. It would be useful to find a method that will allow multiple functions of an oligonucleotide, e.g., its functioning as a primer under one set of conditions and the inhibition of its ability to prime an extension reaction under another set of conditions.

SUMMARY OF THE INVENTION

The present invention provides a method for inhibiting undesired molecular interaction between oligonucleotides and their complexes with polynucleotides and enzymes, including local interactions between their chemical units (nucleotides, amino acids).

The present invention provides a method of inhibiting at least one molecular process in a sample, comprising administering to the sample an oligonucleotide or polynucleotide containing at least one monomeric unit having formula (I):

(I)

wherein A is an organic moiety, n is at least 1, and each X is independently selected from the group consisting of —NRCOCONu, —NHCOCR$_2$CR$_2$CONu, —NHCOCR=CRCONu, and —NHCOSSCONu, wherein each R independently represents H or a substituted or unsubstituted alkyl group, and Nu represents a nucleophile, or a salt of the compound.

DETAILED DESCRIPTION OF PREFERRED EMBODIMENTS

The present invention provides a method of inhibiting at least one molecular process in a sample, comprising administering to the sample an oligonucleotide or polynucleotide containing at least one monomeric unit having formula (I):

(I)

wherein A is an organic moiety, n is at least 1, and each X is independently selected from the group consisting of —NRCOCONu, —NHCOCR$_2$CR$_2$CONu, —NHCOCR=CRCONu, and —NHCOSSCONu, wherein each R independently represents H or a substituted or unsubstituted alkyl group, and Nu represents a nucleophile, or a salt of the compound.

As used herein, oligonucleotide or polynucleotide refers to a macromolecule consisting of a nucleotide chain, which may be of various lengths, and may contain modifications or substitutions at monomeric units of the chain. Such modifications or substitutions should not exceed 50% of the oligonucleotide or polynucleotide.

In embodiments, the oligonucleotide or polynucleotide of the present invention may be modified or substituted at from 1–20 bases, 1–10 bases, such as 1–5 bases, for example 1–2 bases.

Group X may be in various quantities such as 1, 2, 3, 4, 5, 6, 7, 8, 9, 10, 11, 12 or more such groups. In embodiments, multiple X groups is preferable.

Nucleosides, nucleotides and modified nucleosides and nucleotides may be used as organic moieties in the present invention. Non-nucleosides or non-nucleotides may also be used as organic moieties in the present invention. Suitable non-nucleosides or non-nucleotides of the present invention include, but are not limited to, a substituted or unsubstituted alkane, such as an alkane having from 3 to 100 carbon atoms, preferably from 3 to 20 carbon atoms and more preferably from 3 to 12 carbon atoms; a substituted or unsubstituted cycloalkane, such as a cycloalkane having from 3 to 12 carbon atoms in a cycle, preferably from 4 to 8 carbon atoms in a cycle and more preferably from 5 to 6 carbon atoms in a cycle; and a substituted or unsubstituted heterocyclic compound, such as a heterocyclic compound having from 3 to 20 carbon atoms in a cycle, preferably from 3–14 carbon atoms in a cycle. The compound may be substituted with at least one substituent, such as substituents selected from the group consisting of a hydroxy group, a protected hydroxy group and a halogen.

In embodiments of the invention, the nucleophile is selected from the group consisting of compounds having an —O$^-$, an amino group (—NH$_2$), a primary amino group (—NRH) and a secondary amino group (—NR$_2$). Suitable nucleophiles are, for example, listed in Table AA herein.

In embodiments, R may be a substituted or unsubstituted alkyl group. The alkyl group may preferably have from 1 to 15, more preferably from 1 to 12, and even more preferably from 1 to 6 carbon atoms.

Other suitable compounds and methods of synthesizing such compounds are disclosed in U.S. Pat. No. 5,902,879 to Polouchine; U.S. patent application Ser. No. 09/655,317, filed Sep. 5, 2000, to Polouchine; and U.S. patent application Ser. No. 09/655,316, filed Sep. 5, 2000, to Polouchine, the entire disclosures of which are hereby incorporated by reference.

In particular, suitable monomers include compounds of the formula II:

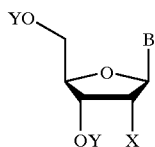

(II)

wherein B is purine or pyrimidine moiety, and each Y independently represents H, a group that protects a hydroxy group, a $(PO_3)_m^{-2}$ group wherein m is an integer of 1–3, a group reactive to link hydroxy groups, or a phosphodiester linkage to another monomer of said oligonucleotide or polynucleotide, and X is selected from the group consisting of —NRCOCONu, —NHCOCR$_2$CR$_2$CONu, —NHCOCR=CRCONu, and —NHCOSSCONu, wherein each R independently represents H or a substituted or unsubstituted alkyl group, and Nu represents a nucleophile.

The present invention will now be discussed by way of example. The following examples are meant to be illustrative not limiting.

EXAMPLES

Example 1

Melting of Modified Oligonucleotides

The following oligonucleotides (SEQ ID NOS: 1–6 from top to bottom) have been synthesized (length 21 bases each, T7 and T7c are complementary and can form perfect duplex):

Oligonucleotides:

| Name | Sequence | position of $U^s$ starting from the 3' end |
|---|---|---|
| T7 | 5'-GTA-ATA-CGA-CTC-ACT-ATA-GGG-3' | none |
| T71 | 5'-GTA-ATA-CGA-CU$^s$C-ACT-ATA-GGG-3' | 11 |
| T72 | 5'-GU$^s$A-ATA-CGA-CTC-ACT-ATA-GGG-3' | 20 |
| T74 | 5'-GU$^s$A-AU$^s$A-CGA-CU$^s$C-ACU$^s$-AU$^s$A-GGG-3' | 5, 7, 10, 17, 20 |
| T7c | 5'-CCC-TAT-AGT-GAG-TCG-TAT-TAC-3' | none |
| T7c3 | 5'-CCC-TAT-AGT-GAG-TCG-TAT-U$^s$AC-3' | 3 | where $U^s$ is 2'-succinimido-2'-deoxyuridine. After synthesis, oligonucleotides have been reacted with different modifiers (see Table AA), deblocked and PAGE purified.

TABLE AA

Partial list of potential modifiers

| Modifier No. | Name | Structure | FW |
|---|---|---|---|
| 1 | Hydroxide Anion | OH— | 17.01 |
| 2 | Ammonia | NH$_3$ | 17.03 |
| 3 | Hydrazine | NH$_2$NH$_2$ | 32.04 |
| 4 | Methylamine | NH$_2$CH$_3$ | 31.06 |
| 5 | Butylamine | NH$_2$(CH$_2$)$_3$CH$_3$ | 73.14 |
| 6 | Dodecylamine | NH$_2$(CH$_2$)$_{11}$CH$_3$ | 185.35 |
| 7 | Ethanolamine | NH$_2$CH$_2$CH$_2$OH | 61.08 |
| 8 | 4-Amino-1-butanol | NH$_2$(CH$_2$)$_4$OH | 89.14 |
| 9 | 6-Amino-1-hexanol | NH$_2$(CH$_2$)$_6$OH | 117.19 |
| 10 | Ethylenediamine | NH$_2$CH$_2$CH$_2$NH$_2$ | 60.10 |
| 11 | 1,4-Diaminobutane | NH$_2$(CH$_2$)$_4$NH$_2$ | 88.15 |
| 12 | Hexamethelenediamine | NH$_2$(CH$_2$)$_6$NH$_2$ | 116.21 |
| 13 | 3-Dimethylaminopropylamine | NH$_2$(CH$_2$)$_3$N(CH$_3$)$_2$ | 102.18 |
| 14 | N,N-Dimethylethylenediamine | NH$_2$CH$_2$CH$_2$N(CH$_3$)$_2$ | 88.15 |
| 15 | Diethylenetriamine | NH$_2$(CH$_2$)$_2$NH(CH$_2$)$_2$NH$_2$ | 103.17 |
| 16 | N'-Isopropyldiethylenetriamine | NH$_2$(CH$_2$)$_2$NH(CH$_2$)$_2$NHCH(CH$_3$)$_2$ | 145.25 |
| 17 | Tris(2-aminoethyl)amine | N(CH$_2$CH$_2$NH$_2$)$_3$ | 146.23 |
| 18 | Triethylenetetramine | NH$_2$(CH$_2$)$_2$NH(CH$_2$)$_2$NH(CH$_2$)$_2$NH$_2$ | 146.23 |
| 19 | 4,7,10-Trioxa-1,13-tridecane-diamine | H$_2$N–(CH$_2$)$_3$–O–(CH$_2$)$_2$–O–(CH$_2$)$_2$–O–(CH$_2$)$_3$–NH$_2$ | 220.31 |
| 20 | 2-(Methylthio)ethylamine | NH$_2$CH$_2$CH$_2$SCH$_3$ | 91.18 |
| 21 | Cystamine | NH$_2$CH$_2$CH$_2$S—SCH$_2$CH$_2$NH$_2$ | 152.28 |
| 22 | Histamine | H$_2$N–CH$_2$CH$_2$–(imidazole) | 111.15 |

TABLE AA-continued

Partial list of potential modifiers

| Modifier No. | Name | Structure | FW |
| --- | --- | --- | --- |
| 23 | Benzylamine | H₂N-CH₂-C₆H₅ | 107.16 |
| 24 | 1-Aminohomopiperidine | H₂N-N(homopiperidine ring) | 114.19 |
| 25 | Tetrahydrofurfurylamine | H₂N-CH₂-(tetrahydrofuran) | 101.15 |
| 26 | 1,12-Diaminododecane | $NH_2(CH_2)_{12}NH_2$ | 200.37 |
| 27 | 2-Aminoethanethiol (cysteamine) | $NH_2CH_2CH_2SH$ | 77.15 |
| 28 | Allylamine | $H_2N-CH_2-CH=CH_2$ | 57.10 |
| 29 | Spermine | $NH_2(CH_2)_3NH(CH_2)_4NH(CH_2)_3NH_2$ | 202.35 |
| 30 | Spermidine | $NH_2(CH_2)_4NH(CH_2)_3NH_2$ | 145.25 |
| 31 | 3-Amino-1,2-propanediol (+/−) | H₂N-CH₂-CH(OH)-CH₂-OH | 91.11 |
| 32 | | H₂N—NH-C(=O)-CH₂-(thymin-1-yl) | 198.18 |
| 33 | 5′-Amino-5′-deoxy-thymidine | (5′-amino-5′-deoxythymidine structure) | 241.25 |
| 34 | | H₂N-CH₂CH₂-NH-C(=O)-CH₂-(thymin-1-yl) | 226.23 |
| 35 | 1-(3-Aminopropyl)-imidazole | H₂N-(CH₂)₃-imidazole | 125.17 |
| 36 | 1,3-Diaminopropane | $NH_2(CH_2)_3NH_2$ | 74.12 |

TABLE AA-continued

Partial list of potential modifiers

| Modifier No. | Name | Structure | FW |
|---|---|---|---|
| 37 | Dansyl cadaverine | 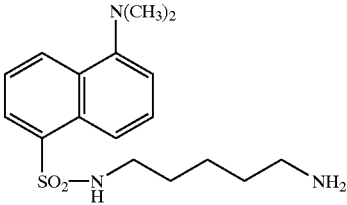 | 335.47 |

A pair of complementary oligonucleotides, each at the concentration 0.1 $A_{260}$ optical units, has been combined in buffer 10 mM Tris-HCl (pH8 at 25° C.), 2 mM $MgCl_2$ in total volume 400 µl, heated to 95° C., cooled to room temperature, and used in melting experiments. Table AB shows the effect of position, number and type of modifications on melting temperature ($T_m$) and width of melting.

TABLE AB

Melting temperature $T_m$ of duplexes with and without modifications

| position of $U^s$ in T7 oligo | Modifier No. | position of $U^s$ in T7c oligo | Modifier No. | $T_m$, ° C. | Change in $T_m$ due to modifications | Width of transition, ° C. |
|---|---|---|---|---|---|---|
| none | | none | | 56.5 | 0.0 | 11.6 |
| 11 | 1 | none | | 52.8 | −3.7 | 8.2 |
| 11 | 3 | none | | 43.7* | −12.8 | 14.3 |
| 11 | 3 | none | | 51.9** | −4.6 | 9.8 |
| 11 | 4 | none | | 52.8 | −3.7 | 8.2 |
| 11 | 6 | none | | 52.9 | −3.6 | 8.3 |
| 11 | 7 | none | | 53.0 | −3.5 | 9.0 |
| 11 | 10 | none | | 53.4 | −3.1 | 9.2 |
| 11 | 14 | none | | 53.9 | −2.6 | 8.5 |
| 11 | 17 | none | | 53.2 | −3.3 | 8.2 |
| 11 | 19 | none | | 52.9 | −3.6 | 8.2 |
| 11 | 28 | none | | 53.0 | −3.5 | 8.1 |
| 11 | 29 | none | | 54.2 | −2.3 | 8.1 |
| 11 | 30 | none | | 53.4 | −3.1 | 8.1 |
| 11 | 31 | none | | 53.1 | −3.4 | 8.3 |
| 11 | 35 | none | | 53.2 | −3.3 | 8.4 |
| 20 | 1 | none | | 58.4 | 1.9 | 8.2 |
| 20 | 3 | none | | 47.9* | −8.6 | 10.1 |
| 20 | 3 | none | | 57.4** | 0.9 | 9.0 |
| 20 | 4 | none | | 57.8 | 1.3 | 8.3 |
| 20 | 6 | none | | 58.5 | 2.0 | 8.2 |
| 20 | 7 | none | | 58.2 | 1.7 | 9.3 |
| 20 | 10 | none | | 58.6 | 2.1 | 9.7 |
| 20 | 14 | none | | 59.1 | 2.6 | 9.5 |
| 20 | 19 | none | | 58.1 | 1.6 | 8.9 |
| 20 | 28 | none | | 58.1 | 1.6 | 9.2 |
| 20 | 29 | none | | 58.7 | 2.2 | 8.8 |
| 20 | 30 | none | | 57.9 | 1.4 | 7.7 |
| 20 | 31 | none | | 58.2 | 1.7 | 9.5 |
| 20 | 35 | none | | 58.2 | 1.7 | 9.2 |
| none | | 3 | 1 | 54.2 | −2.3 | 13.3 |
| none | | 3 | 3 | 53.7 | −2.8 | 14.2 |
| none | | 3 | 7 | 54.2 | −2.3 | 13.8 |
| none | | 3 | 19 | 54.8 | −1.7 | 13.1 |
| none | | 3 | 29 | 55.4 | −1.1 | 13.2 |
| 20 | 1 | 3 | 1 | 58.0 | 1.5 | 9.0 |
| 20 | 1 | 3 | 10 | 57.0 | 0.5 | 9.8 |
| 20 | 10 | 3 | 10 | 57.7 | 1.2 | 10.0 |
| 20 | 14 | 3 | 1 | 58.2 | 1.7 | 9.1 |
| 20 | 29 | 3 | 1 | 57.7 | 1.2 | 8.4 |
| 5,7,10,17,20 | 1 | none | | 40.1 | −16.4 | 9.8 |
| 5,7,10,17,20 | 3 | none | | 28.9 | −27.6 | 14.4 |
| 5,7,10,17,20 | 4 | none | | 39.5 | −17.0 | |
| 5,7,10,17,20 | 7 | none | | 38.1 | −18.4 | 9.7 |
| 5,7,10,17,20 | 12 | none | | 41.1 | −15.4 | |
| 5,7,10,17,20 | 14 | none | | 43.1 | −13.4 | 9.1 |
| 5,7,10,17,20 | 17 | none | | 44.6 | −11.9 | |
| 5,7,10,17,20 | 19 | none | | 38.6 | −17.9 | |
| 5,7,10,17,20 | 29 | none | | 46.3 | −10.2 | 9.8 |
| 5,7,10,17,20 | 30 | none | | 41.1 | −15.4 | |
| 5,7,10,17,20 | 31 | none | | 39.5 | −17.0 | |
| 5,7,10,17,20 | 35 | none | | 39.8 | −16.7 | |

*)Two transitions have been observed.
*$T_m$ of the first transition,
**$T_m$ of the second transition.

Data shows that presence of modified nucleotides affects melting temperature. The effect is especially pronounced when five nucleotides per oligonucleotide have been modified. The change in $T_m$ in this case depends significantly on the type of modifier.

Example 2

Inhibition of Non-Specific Annealing and Primer Extension Using Multiply Modified Oligonucleotides The following oligonucleotides (SEQ ID NOS: 7–12 from top to bottom) have been synthesized:

Oligonucleotides:

| Name | Sequence | Position of $U^s$ starting from the 3' end |
|---|---|---|
| PFOR0001 | AAACGACGGCCAGTGAATTGTAATACGAC TCACTATAGGG | none |
| PFOR0002 | AAACGACGGCCAGTGAATTGTAATACGAC $U^s$CACTATAGGG | 11 |
| PFOR0003 | AAACGACGGCCAGTGAATTGTAAU$^s$ACGAC $U^s$CACTAU$^s$AGGG | 5, 11, 17 |
| PFOR0004 | AAACGACGGCCAGU$^s$GAATTGU$^s$AAU$^s$ACGA CU$^s$CACU$^s$AU$^s$AGGG | 5, 7, 11, 17, 20, 27 |
| PFOR0005 | cccccaaaaaCCCTATAGTGAGTCGTATTACAA TTCACTGGCCGTCGTTTtt | none |
| PFOR0006 | aaaaaccccccCCCTATAGTGAGTCGTATTACtttttttt tttttttttttttt | none | where $U^s$ is 2'-succinimido-2'-deoxyuridine. Oligonucleotides PFOR0002–PFOR0004 differ from oligonucleotide PFOR0001 by 1, 3 or 6 positions where T was substituted for $U^s$. Oligonucleotide PFOR0005 is 52 bases long and has 40 bases that are complementary to PFOR0001. Oligonucleotide PFOR0006 is 52 bases long and has 20 bases that are complementary to the 3' proximal 20 bases of PFOR0001. After synthesis, oligonucleotides PFOR0002–PFOR0004 have been reacted with Hydroxide Anion or N,N-Dimethylethylenediamine (modifier No. 1 or 14, Table AA), deblocked and PAGE purified.

A pair of complementary oligonucleotides, each at the concentration 0.1 A260 optical units, has been combined in buffer 10 mM Tris-HCl (pH8 at 25° C.), 2 mM MgCl$_2$ in total volume 400 μl, heated to 95° C., cooled to room temperature, and used in melting experiments. Table FF shows the effect of the number of modifications on melting temperature ($T_m$).

TABLE FF

Melting temperature $T_m$ of duplexes with and without modifications

| Oligo-nucleotide Name | Position of $U^s$ | Modifier | $T_m$, °C. of duplex with PFOR0005 | $T_m$, °C. of duplex with PFOR0006 |
|---|---|---|---|---|
| PFOR0001 | none | | 74.3 | 59.0 |
| PFOR0007 | 11 | 1 | 71.5 | 53.6 |
| PFOR0008 | 5, 11, 17 | 1 | 69.6 | 47.7 |
| PFOR0009 | 5, 7, 11, 17, 20, 27 | 1 | 58.0 | 33.4 |
| PFOR0010 | 11 | 14 | 71.5 | 53.5 |
| PFOR0011 | 5, 11, 17 | 14 | 69.5 | 47.5 |
| PFOR0012 | 5, 7, 11, 17, 20, 27 | 14 | 59.9 | 34.2 |

Data shows that presence of modified nucleotides affects melting temperature. The effect is especially pronounced when multiple nucleotides per oligonucleotide have been modified.

The following experiments have been conducted to determine the ability of primers to discriminate between templates that have identical 20 bases-long sequences for primer annealing. Oligonucleotides PFOR0005 and PFOR0006 have been mixed and each could potentially serve as a template for priming by oligonucleotides PFOR0001, PFOR0007–PFOR0012. If only PFOR0005 is used as a template in a sequencing reaction, one would expect to read a sequence tttttggggg (SEQ ID NO: 71) from sequencing traces, if only PFOR0006 is used as a template, one would expect to read a sequence gggggtttt (SEQ ID NO: 72) from sequencing traces. If both PFOR0005 and PFOR0006 are used as templates in a sequencing reaction, one would expect to have a mixed signal on sequencing traces. The sequencing reaction contained 5 pmole of each template (PFOR0005 and PFOR0006), 10 pmole of one of the primers (PFOR0001, PFOR0007–PFOR0012), 2 μl Big Dye Terminator Ready Reaction Mix (Applied Biosystems). Reaction volume was 5 μl. Reactions were done with the following thermal conditions: denaturation at 95° C. for 2 min, annealing at 55° C. for 30 sec and extension at 60° C. for 4 min. Samples were analyzed on 12 cm 10% polyacrylamide gel on ABI PRISM 377 Sequencer. Primer PFOR0001 hybridized to both templates at these conditions. The sequencing reaction occurred from both templates (Panel A). Primer PFOR0009, however, hybridized only to PFOR0005 template containing all 40 complementary bases. The sequencing reaction was only from this template and the expected read tttttggggg (SEQ ID NO: 71) was obtained (Panel B). Table FG summarizes data for all primers used.

Panel A. Sequencing traces for primer PFOR0001 and a mix of PFOR0005 and PFOR0006 templates. Each peak corresponds to the presence of a primer extension product that terminates on T or G and differs by one nucleotide in length.

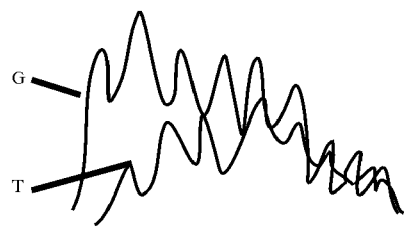

Panel B. Sequencing traces for primer PFOR0007 and a mix of PFOR0005 and PFOR0006 templates. Each peak corresponds to the presence of a primer extension product that terminates on T or G and differs by one nucleotide in length. These traces allow one to read a sequence of the template used by the primer, i.e., tttttggggg (SEQ ID NO: 71).

TABLE FG

Selectivity of primer extension on the mixture of two templates

| Primer Name | position of Us | modifier | Templates used by the primer |
|---|---|---|---|
| PFOR0001 | none | | Both PFOR0005 and PFOR0006 |
| PFOR0007 | 11 | 1 | Both PFOR0005 and PFOR0006 |
| PFOR0008 | 5, 11, 17 | 1 | Only PFOR0005 |
| PFOR0009 | 5, 7, 11, 17, 20, 27 | 1 | Only PFOR0005 |
| PFOR0010 | 11 | 14 | Both PFOR0005 and PFOR0006 |
| PFOR0011 | 5, 11, 17 | 14 | Only PFOR0005 |
| PFOR0012 | 5, 7, 11, 17, 20, 27 | 14 | Only PFOR0005 |

Data shows that presence of more than one modified nucleotide in the primer inhibits the utilization of the sequence, which is only partially complementary to the primer, as a template for the sequencing reaction, while it does not preclude the sequencing reaction from the site that has a complementary sequence to the whole primer.

Example 3

Melting of Multiply Modified Oligonucleotides

The following oligonucleotides (SEQ ID NOS: 13–18 from top to bottom) have been synthesized (length 31 bases each, DMEL0001 and DMEL0002 are complementary and can form perfect duplex):
Oligonucleotides:

| Name | Sequence | position of $U^s$ starting from the 3' end |
|---|---|---|
| DMEL0001 | ggctagctccctgccagcagccgcggtaata | none |
| FSUC0403 | ggctagctccctgccagcagccgcggU$^s$aata | 5 |
| FUSC0404 | ggcU$^s$agctccctgccagcagccgcggU$^s$aata | 5, 28 |
| FSUC0405 | ggcU$^s$agcU$^s$ccU$^s$gccagcagccgcggU$^s$aata | 5, 20, 24. 28 |
| DMEL0002 | tattaccgcggctgctggcagggagctagcc | none |
| FSUC0406 | tatU$^s$accgcggcU$^s$gcU$^s$ggcagggagcU$^s$agcc | 5, 16, 19, 28 | where $U^s$ is 2'-succinimido-2'-deoxyuridine. After synthesis, oligonucleotides have been reacted with Hydroxide Anion (modifier No. 1, Table AA), deblocked and PAGE purified.

A pair of complementary oligonucleotides, each at the concentration 0.1 $A_{260}$ optical units, has been combined in buffer 10 mM Tris-HCl (pH8 at 25° C.), 2 mM MgCl$_2$ in total volume 400 μl, heated to 95° C., cooled to room temperature, and used in melting experiments. Table CC shows the effect of the number of modifications on melting temperature ($T_m$).

TABLE CC

Melting temperature $T_m$ of duplexes with and without modifications

| position of $U_s$ in DMEL0001 oligo | position of $U^s$ in DMEL0002 oligo | $T_m$, ° C. | Change in $T_m$ due to modifications |
|---|---|---|---|
| none | none | 79.1 | 0.0 |
| 5 | none | 78.3 | −0.8 |
| 5, 28 | none | 76.9 | −2.1 |
| 5, 20, 24, 28 | none | 70.0 | −9.0 |
| none | 5, 16, 19, 28 | 69.6 | −9.5 |
| 5 | 5, 16, 19, 28 | 68.5 | −10.5 |
| 5, 28 | 5, 16, 19, 28 | 67.5 | −11.5 |
| 5, 20, 24, 28 | 5, 16, 19, 28 | 59.5 | −19.6 |

Data show that presence of modified nucleotides affects melting temperature. The effect is especially pronounced when multiple nucleotides per oligonucleotide have been modified.

Example 4

Melting of Short Modified Oligonucleotides

The following oligonucleotides have been synthesized (length 10 bases each): $T_{10}$ (SEQ ID NO: 19), $T_8U^sT$ (SEQ ID NO: 20), $T_7U^sT_2$ (SEQ ID NO: 21), $T_6U^sT_3$ (SEQ ID NO: 22), $T_5U^sT_4$ (SEQ ID NO: 23), $T_2U^sT_7$ (SEQ ID NO: 24), $TU^sT_8$ (SEQ ID NO: 25), $U^sT_9$ (SEQ ID NO: 26), where T is 2'-deoxyT, $U^s$ is 2'-succinimido-2'-deoxyuridine. After synthesis, oligonucleotides have been reacted with Hydroxide Anion (modifier No. 1, Table AA) and deblocked. $T_{10}$ oligonucleotide with or without modified nucleotide has been combined with $dA_{18}$ oligonucleotide, each at the concentration 0.1 $A_{260}$ optical units, in buffer 10 mM Tris-HCl (pH8 at 25° C.), 2 or 10 mM MgCl$_2$ in total volume 400 μl, and used in melting experiments. Table DD shows the effect of the position of modifications on melting temperature ($T_m$).

TABLE DD

Melting temperature $T_m$ of duplexes with and without modifications

| position of $U^s$ in $T_{10}$ oligo | $T_m$, ° C., 2 mM Mg | $T_m$, ° C., 10 mM Mg |
|---|---|---|
| none | 31.0 | |
| 2 | 22.7 | 29.2 |
| 3 | 16.0 | 23.2 |
| 4 | | 17.9 |

TABLE DD-continued

Melting temperature $T_m$ of duplexes with and without modifications

| position of $U^s$ in $T_{10}$ oligo | $T_m$, °C., 2 mM Mg | $T_m$, °C., 10 mM Mg |
|---|---|---|
| 5 | | 16.1 |
| 8 | 15.6 | |
| 9 | 21.6 | |
| 10 | 25.5 | |

Data shows that presence of modified nucleotide significantly affects melting temperature and that the effect is dependent on the position of modification in the oligonucleotide.

The results show that significant inhibition of formation of relatively short duplexes can be achieved by using only one modification in an oligonucleotide and placing it within a site of potential secondary structure or duplex formation.

Example 5

Inhibition of Primer Extension Using Modified Nucleotides in the Template Strand To test the effect of modified nucleotides that are present in the template strand in front the polymerase active site or behind its active site (under the primer), the following oligonucleotides (SEQ ID NOS: 27–29, 1 and 30–33 from top to bottom) have been synthesized:
Oligonucleotides:

| Name | Sequence | Length, bases |
|---|---|---|
| PGEZ0001 | attGTAATACGACTCACTATA | 21 |
| PGEZ0002 | ttGTAATACGACTCACTATAG | 21 |
| PGEZ0003 | tGTAATACGACTCACTATAGG | 21 |
| T7 | GTAATACGACTCACTATAGGG | 21 |
| PGEZ0004 | cttttcgCCCTATAGTGAGTCGTATTAC | 28 |
| PGEZ0111 | cttU$^s$tcgCCCTATAGTGAGTCGTATTAC | 28 |
| PGEZ0012 | cU$^s$U$^s$U$^s$tcgCCCTATAGTGAGTCGTATTAC | 28 |
| PGEZ0013 | cttttcgCCCU$^s$ATAGTGAGTCGTATTAC | 28 | where $U^s$ is 2'-succinimido-2'-deoxyuridine. Any of oligonucleotides PGEZ0001–PGEZ0003 and T7 can form duplexes with any of oligonucleotides PGEZ0004 and PGEZ0011–PGEZ0013 or their modified derivatives. Oligonucleotides PGEZ0011–PGEZ0013 differ from oligonucleotide PGEZ0004 by the number and positions of substitutions of T for $U^s$. After synthesis, oligonucleotides PGEZ0011–PGEZ0013 have been reacted with Hydroxide Anion, Ethanolamine, or 3-Dimethylaminopropylamine (modifier No. 1, 7, or 13, Table AA), deblocked and PAGE purified.

To test the effect of modified nucleotides that are present in the template strand in front of the polymerase active site, we have used T7 oligonucleotide as a primer and modified PGEZ0011 and PGEZ0012 oligonucleotides as templates. PGEZ0004 was used as control template. The sequencing reaction contained 3 pmole of each template and primer oligonucleotides, 2 μL BigDye Terminator Ready Reaction Mix (Applied Biosystems). Reaction volume was 5 μL. Reactions were done with the following thermal conditions: denaturation at 95° C. for 2 min, annealing at 55° C. for 30 sec and extension at 60° C. for 4 min. Samples were analyzed on 12 cm 10% polyacrylamide gel on ABI PRISM 377 Sequencer.

The reactions with templates with one (modifications of PGEZ0011) or three (modifications of PGEZ0012) modified nucleotides produced only three extension products of T7 primer (Table HH). Their sizes were 22, 23 and 24 bases and they terminated on C, G and A, respectfully. No products with 4 or more added nucleotides to T7 primer have been detected. The reaction with non-modified template produced 8 extension products of T7 primer, 7 of them are as expected for template-directed addition of nucleotides by DNA polymerase and the longest one terminated on A and was due to the non-templated addition of a nucleotide by DNA polymerase (Table HH).

We have also detected the products of the non-templated addition of one nucleotide by DNA polymerase to the template oligonucleotides. The electrophoretic mobility of these 29 bases-long products has been found to depend on the number and type of modifications of the nucleotides (Table HH).

TABLE HH

Termination of the primer extension reaction by modified nucleotide in the template strand in front of DNA polymerase active site

| Template Name | Number of $U^s$ | Modifier | Nucleotides added by polymerase to T7 primer | Nucleotides added by polymerase to the template oligonucleotide | Relative electrophoretic mobility of the template oligonucleotide with one nucleotide added by polymerase |
|---|---|---|---|---|---|
| PGEZ0004 | none | | CGAAAAGa | a | 1.000 |
| PGEZ0051 | 1 | 1 | CGA | a | 0.991 |
| PGEZ0052 | 3 | 1 | CGA | a | 0.984 |
| PGEZ0054 | 1 | 7 | CGA | a | 1.005 |
| PGEZ0055 | 3 | 7 | CGA | a | 1.023 |
| PGEZ0057 | 1 | 13 | CGA | a | 1.018 |
| PGEZ0058 | 3 | 13 | CGA | a | 1.085 |

The results demonstrate that primer extension reaction is completely inhibited when DNA polymerase encounters modified nucleotide in the template strand.

To test the effect of modified nucleotides that are present in the template strand behind the polymerase active site (under the primer), we have used modified PGEZ0013 oligonucleotides as templates and T7 and PGEZ0001–PGEZ0003 oligonucleotides as primers. PGEZ0004 was used as a control template. Sequencing reactions and analysis were done as described above.

The results of the experiments are summarized in Table HI. The effect of a nucleotide modification in the template strand that makes the base pair with the primer and that is located at the −4 position from the primer 3′ end has not been detected. Primer extension reaction was inhibited approximately two-fold when a modified nucleotide in the template strand was at the −3 position from the 3′ end of the primer. A 20 to 100 fold inhibition of primer extension reaction was detected when a modified nucleotide in the template strand was at the −2 or −1 position from the 3′ end of the primer. In the latter case, the extent of inhibition was dependent on the type of nucleotide modification.

Oligonucleotides:

| Name | Sequence | position of $U^s$ starting from the 3′ end |
|---|---|---|
| T7 | gtaatacgactcactatagg | none |
| pG3 | ttgtaatacgactcactaU$^s$ag | 3 |
| pG4 | tgtaatacgactcactaU$^s$agg | 4 |
| pG5 | gtaatacgactcactaU$^s$aggg | 5 |
| pG6 | tgtaatacgactcacU$^s$atagg | 6 |
| pG7 | gtaatacgactcacU$^s$ataggg | 7 |
| pG8 | atacgactcactaU$^s$agggcga | 8 |
| pG9 | ttgtaatacgacU$^s$cactatag | 9 |
| pG10 | tgtaatacgacU$^s$cactatagg | 10 |
| T72 | gU$^s$aatacgactcactataggg | 20 | where $U^s$ is 2′-succinimido-2′-deoxyuridine. After synthesis, oligonucleotides have been reacted with different modifiers (see Table AA), deblocked and PAGE purified.

To test the effect of modified nucleotides that are present in a primer, we have used T7 non-modified oligonucleotide and pG3-pG10 and T72 oligonucleotides modified with

TABLE HI

Inhibition of the primer extension reaction by modified nucleotide in the template strand behind DNA polymerase active site

| Primer | Template | Modifier | Position of modified base relative to the 3′ end of the primer | First five nucleotides added by polymerase to the primer | Relative yield of the primer extension products | Nucleotides added by polymerase to the template oligo-nucleotide | Relative electrophoretic mobility of the template oligonucleotide with one nucleotide added by polymerase |
|---|---|---|---|---|---|---|---|
| T7 | PGEZ-0004 | none | | CGAAA | 1 | a | 1.000 |
| T7 | PGEZ-0053 | 1 | −4 | CGAAA | 1 | a | 0.999 |
| T7 | PGEZ-0056 | 7 | −4 | CGAAA | 1 | a | 1.008 |
| T7 | PGEZ-0059 | 13 | −4 | CGAAA | 1 | a | 1.012 |
| PGEZ-0001 | PGEZ-0053 | 1 | −3 | GCGAA | 0.5 | Aa | 0.999 |
| PGEZ-0001 | PGEZ-0056 | 7 | −3 | GCGAA | 0.5 | Aa | 1.007 |
| PGEZ-0001 | PGEZ-0059 | 13 | −3 | GCGAA | 0.5 | Aa | 1.013 |
| PGEZ-0002 | PGEZ-0053 | 1 | −2 | GGCGA | 0.03 | AAa | 0.993 |
| PGEZ-0002 | PGEZ-0056 | 7 | −2 | GGCGA | 0.05 | AAa | 1.005 |
| PGEZ-0002 | PGEZ-0059 | 13 | −2 | GGCGA | 0.01 | AAa | 1.010 |
| PGEZ-0003 | PGEZ-0053 | 1 | −1 | GGGCG | 0.03 | AATa | 0.999 |
| PGEZ-0003 | PGEZ-0056 | 7 | −1 | GGGCG | 0.05 | AATa | 1.004 |
| PGEZ-0003 | PGEZ-0059 | 13 | −1 | GGGCG | 0.01 | AATa | 1.013 |

The results demonstrate that using a modified nucleotide in the template strand and placing it in the proximity of the polymerase active site inhibits a primer extension reaction.

Example 6

Effect of the Type and Position of the Modified Nucleotide on the Yield of Sequencing Reaction The following oligonucleotides (SEQ ID NOS: 1 and 34–42 from top to bottom) have been synthesized (length 21 bases each):

Hydroxide Anion or Spermine (modifier No. 1 or 29, Table AA) as a primer and pGEM-3zfp plasmid DNA (Promega) as a template. The sequencing reaction contained 3 pmole of primer oligonucleotide, 50 ng pGEM DNA, 2 μL BigDye Terminator Ready Reaction Mix (Applied Biosystems). Reaction volume was 5 μL. Cycle sequencing reactions were done with the following thermal conditions: denaturation at 95° C. for 2 min, {denaturation at 95° C. for 5 sec, annealing at 55° C. for 30 sec and extension at 60° C. for 4 min} repeat 50 times, cool to 4° C. Samples were analyzed on 36 cm 4.5% polyacrylamide gel on ABI PRISM 377 Sequencer.

Modified primers pG5-pG10 and T72 and non-modified T7 primer generated sequencing traces of pGEM DNA that were nearly identical. We have not detected any differences in the yield of primer extension products. Thus, nucleotide modifications in the primer that are at least 5 bases from the 3′ end may be used in sequencing reaction.

The yield of modified pG3 and pG4 primer extension products was 5 to 15 than the yield of T7 primer extension products. This result indicates that modifications of nucleotides near the 3' end may inhibit a primer extension reaction.

To assess the effect of nucleotide modifications near the 3' end of the oligonucleotide on the primer extension reaction, we have prepared an extended set of modified pG3 and pG4 oligonucleotides and tested their effect on a cycle sequencing reaction. Sequencing reactions have been assembled essentially as described above. In reactions we have also added 0.3 mM manganese citrate, or 0.1 mM deaza-dGTP, or both. The effects of the type of nucleotide modifications, its position in the primer and buffer conditions on the yield of a cycle sequencing reaction is summarized in Table JJ. In the Table, the yield of cycle sequencing reactions has been normalized to the yield of reaction obtained with T7 primer in standard buffer conditions.

Oligonucleotides:

| Name | Sequence | position of $C^m$ starting from the 3' end |
|---|---|---|
| DMEL0008 | tgtaaaacgacggccagt | none |
| CMOX0001 | tgtaaaacgacggC$^m$agt | 4 |
| CMOX0002 | tgtaaaacgacggC$^m$cagt | 5 |
| CMOX0003 | tgtaaaacgaC$^m$ggccagt | 8 |
| CMOX0004 | tgtaaaaC$^m$gacggccagt | 11 |
| CMOX0005 | tgtaaaaC$^m$gacggC$^m$cagt | 5, 11 |
| DMEL0011 | caggaaacagctatgacc | none |
| CMOX0006 | caggaaacagctatgaC$^m$c | 2 |
| CMOX0007 | caggaaacagC$^m$tatgacc | 8 |

TABLE JJ

Yield of the primer extension reaction

| modifier | No additives | + deaza-dGTP | + MnCit | + MnCit + deaza-dGTP | No additives | + deaza-dGTP | + MnCit | + MnCit + deaza-dGTP |
|---|---|---|---|---|---|---|---|---|
| None, control T7 primer | 1 | 0.5 | 1.2 | 1.2 | | | | |
| | \multicolumn{4}{c}{Yield of primer extension products. Modifications of pG3 oligonucleotide precursor} | \multicolumn{4}{c}{Yield of primer extension products. Modifications of pG4 oligonucleotide precursor} | | | | |
| 1 | 0.1 | 0.4 | 1.3 | 0.9 | 0.1 | 0.2 | 0.5 | 0.2 |
| 3 | 0.0 | 0.0 | 0.1 | 0.2 | 0.0 | 0.0 | 0.1 | 0.0 |
| 4 | 0.0 | 0.2 | 1.5 | 0.7 | 0.2 | 0.3 | 1.1 | 0.3 |
| 6 | 0.2 | 0.5 | 1.4 | 1.2 | 0.1 | 0.2 | 0.5 | 0.4 |
| 7 | 0.1 | 0.3 | 1.4 | 0.3 | | | | |
| 10 | 0.2 | 0.3 | 1.1 | 1.1 | 0.1 | 0.2 | 0.5 | 0.4 |
| 14 | 0.1 | 0.0 | 0.9 | 0.6 | 0.1 | 0.1 | 1.0 | 0.6 |
| 17 | 0.4 | 0.5 | 0.6 | 0.6 | 0.1 | 0.2 | 0.4 | 0.3 |
| 19 | 0.1 | 0.3 | 1.2 | 1.0 | 0.0 | 0.1 | 0.5 | 0.2 |
| 22 | 0.1 | 0.2 | 0.9 | 0.7 | 0.0 | 0.0 | 0.1 | 0.1 |
| 29 | 0.2 | 0.5 | 1.2 | 1.0 | 0.1 | 0.1 | 0.7 | 0.3 |
| 31 | 0.1 | 0.2 | 1.2 | 0.7 | 0.0 | 0.0 | 0.3 | 0.2 |
| 35 | 0.0 | 0.2 | 0.9 | 0.7 | 0.0 | 0.1 | 0.5 | 0.3 |
| 36 | 0.1 | 0.2 | 1.0 | 0.6 | 0.0 | 0.2 | 0.7 | 0.4 |

The results show that it is possible to select nucleotide modification near the 3' end of the oligonucleotide that will inhibit primer extension reaction by DNA polymerase. Moreover, it is possible to select a modified oligonucleotide (e.g., with 1-(3-Aminopropyl)-imidazole, modifier #35) that will be able to serve as a primer under one set of conditions (+MnCit) while not act as a primer under other conditions (for example, no additives).

Example 7

Effect of the Type and Position of Modified Cytosine on the Yield of a Sequencing Reaction The following oligonucleotides (SEQ ID NOS: 43–51 from top to bottom) have been synthesized (length 18 bases each):

where $C^m$ is 2'-methoxyoxalamido-2'-deoxycytidine. After synthesis, oligonucleotides have been reacted with different modifiers (see Table AA), deblocked and PAGE purified.

To test the effect of modified 2'-methoxyoxalamido-2'-deoxycytidine nucleotides that are present in a primer, we have used DMEL0008 and DMEL0011 non-modified oligonucleotides and CMOX0001–CMOX0007 oligonucleotides modified with Hydroxide Anion or Ethanolamine (modifier No. 1 or 7, Table AA) as primers and pGEM-3zfp plasmid DNA as a template. The sequencing reaction contained 3 pmole of primer oligonucleotide, 200 ng pGEM DNA, 2 μL BigDye Terminator Ready Reaction Mix. Reaction volume was 5 μL. Cycle sequencing reactions were done with the following thermal conditions: denaturation at 95° C. for 2 min, {denaturation at 95° C. for 5 sec, annealing at 55° C. for 30 sec and extension at 60° C. for 4 min} repeat 30 times, cool to 4° C. Samples were analyzed on 36 cm 4.5% polyacrylamide gel on ABI PRISM 377 Sequencer.

Traces with identifiable sequences have been obtained for all non-modified and modified primers except CMOX0006. The yield of the sequencing reaction with modified CMOX0005 primers was greatly reduced compared to a non-modified control primer. The effect of the type of nucleotide modifications and its position in the primer on the yield of cycle sequencing reaction is summarized in Table KK. In the Table, the yield of cycle sequencing reactions with modified primers has been normalized to the yield of the reaction obtained with corresponding control primers.

TABLE KK

Yield of the primer extension reaction

| modi-fier | DMEL00081 | | | | | DMEL00111 | |
|---|---|---|---|---|---|---|---|
| | CMOX-0001 | CMOX-0002 | CMOX-0003 | CMOX-0004 | CMOX-0005 | CMOX-0006 | CMOX-0007 |
| 1 | 0.8 | 0.6 | 0.6 | 1.4 | 0.3 | 0.0 | 0.6 |
| 7 | 0.8 | 0.5 | 0.4 | 0.9 | 0.1 | 0.0 | 1.1 |

The results show that 2'- methoxyoxalamido-2'-deoxycytidine near the 3' end of the oligonucleotide completely inhibits primer extension reaction by DNA polymerase. At the same time, modified nucleotides at least 4 bases away of the 3' end may be used for primer extension.

Example 8

Inhibition of Non-Specific PCR Amplification Associated with a 400-Cycle Sequencing Reaction The following oligonucleotides (SEQ ID NOS: 52 and 53 from to to bottom) have been synthesized (length 35 bases each):
Oligonucleotides:

| Name | Sequence | position of $U^s$ starting from the 3' end |
|---|---|---|
| 35T7 | acggccagtgaattgtaatacgactcactataggg | none |
| 35T7s7 | acggccagtgaattgtaatacgactcacta$U^s$aggg | 5 | where $U^s$ is 2'-succinimido-2'-deoxyuridine. After synthesis, 35T7s7 oligonucleotide has been reacted with Ethanolamine (modifier 7, see Table AA), both oligonucleotides were deblocked and PAGE purified.

As a template for cycle sequencing reaction, BAC DNA containing human SEP15 gene cloned into pBeloBAC11 vector (BAC-5231 library from Genome Systems, clone ID is 16025) was used. The end sequences of the cloned human DNA insert are CAAGCTTGTTTTAAACCATTAGGTT-TAAGGGTGTTTTTA (SEQ ID NO: 73) (on T7 side), and AAGCTTCGGGAACCATGTCTTTAGG-TAAGTGAGGCAACAG (SEQ ID NO: 74) (on SP6 side).

The sequencing reaction contained 30 ng BAC DNA, 0.1 μL ThermoFidelase 2 (Fidelity Systems, Inc.), 0 or 0.1 mM 7-deaza-dGTP, 0.3 mM MnCl$_2$, 2 μL BigDye Terminator Mix (Applied Biosystems) and 10 pmole primer. Reaction volume was 5 μL. Cycle sequencing was done at the following conditions: initial denaturation at 95° C. for 2 min, then 400 cycles with 95° C. for 5 sec and 60° C. for 1.5 min. After cycle sequencing was completed, samples were cooled down to 4° C. Samples were purified from non-incorporated dyes by filtration through Sephadex G-50 in 96 well filter plate (Millipore) according to the manufacturer's protocol, dried in SpeedVac system and resuspended in 3 μL loading buffer. 1 μl from each sample was loaded on 36 cm 5% polyacrylamide gel and analyzed on ABI Prism 377 DNA Sequencer (Applied Biosystems).

The reactions with modified 35T7s7 primer yielded sequence traces with 500 readable bases when either deaza-dGTP was absent or added to the buffer. However, reactions with 35T7 primer produced unidentifiable products that are indicative of non-specific PCR amplification that occurred in conjunction with cycle sequencing. The size of the longest PCR products depends on the reaction additives (Table LL).

TABLE LL

Size of the longest non-specific PCR product generated during cycle sequencing

| | Size of non-specific PCR product, bp | |
|---|---|---|
| Primer | Reactions without deaza-dGTP added | Reactions with deaza-dGTP added |
| 35T7 | 280 | 100 |
| 35T7s7 | none | none |

This example shows a number of advantages of using modified primers in cycle sequencing reactions. First, inhibition of polymerase extension when it reaches a modified nucleotide in the fifth position in the primer may prevent non-specific PCR amplification for as many as 400 thermal cycles, or more, and in the presence of deaza-dGTP. Second, dramatically increased number of cycles allows to reduce consumption of template BAC DNA per reaction from standard 2,000 ng to as low as 30 ng. Third, inhibition of non-desired processes during cycle sequencing due to the incorporated modified nucleotide in the primer allows one to increase the size of the sequencing primer approximately two-fold compared to the standard procedures. The primers with increased length are especially useful for long templates such as BAC and genomic DNA templates.

Example 9

Specific PCR Amplification with Modified Oligonucleotides

The following oligonucleotides (SEQ ID NOS: 54–56 from top to bottom) have been synthesized:
Oligonucleotides:

| Name | Sequence |
|---|---|
| PDYE0023 | $U^s$gtaaaacgacggccagt |
| PDYE0024 | $U^s$caggaaacagctatgacc |
| PDYE0025 | $U^s$cgccaagctatttaggtgaca | where $U^s$ is 2'-succinimido-2'-deoxyuridine. To a CPG bound SUC precursor oligonucleotide (1–3 mg) 40 μl 4,7,10-trioxa-1,13-tridecanediamine (modifier No. 19, Table AA) was added. The reaction mixture was incubated at 70° C. for 30 min. Ethyl alcohol (500 μl) was added. The mixture was vortexed, incubated at 0° C. for 30 min and centrifuged at 13,000 g for 20 min. The alcohol solution was discarded. The precipitate was dissolved in water (150 μl) and the solution was filtered. Saturated aqueous NaCl (30 μl) and ethyl alcohol (600 μl) were sequentially added. The mixture was vortexed, incubated at 0° C. for 30 min and centrifuged at 13,000 g for 20 min. The alcohol solution was discarded. The precipitate was washed with ether (300 μl) and dried.

The dried precipitate was dissolved in water (15 μl). To the solution collidine (5 μl) and 0.05 M solution of a succinimidil ester (NHS-ester) of a dye in DMF (40 μl) were added. The reaction mixture was vortexed and incubated at room temperature for 3–5 hrs. The reaction was quenched with 5 M aqueous ammonium acetate (15 μl). Ethyl alcohol (500 μl) was added. The mixture was vortexed, incubated at 0° C. for 30 min and centrifuged at 13000 g for 20 min. The alcohol solution was discarded. The products were purified by PAGE.

PCR mixture contained 20 ng pGEM-3zfp DNA, 50 pmole of each oligonucleotide, 0.2 mM of each dNTP, 2.5 U AmpliTaq DNA Polymerase, 5 μL GeneAmp 10×PCR Buffer (Applied Biosystems). Reaction volume was 50 μL. PCR was done at the following conditions: initial denaturation at 94 C. for 2 min, then 30 cycles with 92° C. for 40 sec, 60° C. for 40 sec and 72° C. for 1.5 min. After 30 cycl were completed additional extension at 72° C. for 5 min was done. The samples were cooled down to 4° C. 2 μL aliquote from each PCR was diluted 100 times with loading buffer, containing 5 parts deionized formamide and 1 part 25 mM EDTA, 50 mg/ml blue dextran. Before loading on the gel, samples were heated to 95° C. for 2 min, then placed on ice. One microliter from each sample was loaded on the 12 cm 10% polyacryamide gel and analyzed on ABI Prism 377 DNA Sequencer (Applied Biosystems).

Table MM shows fragment sizes, obtained in PCR with two primer pairs used.

TABLE MM

| PCR products obtained with 5' end modified primers | | |
|---|---|---|
| Primer 1 | Primer 2 | PCR Fragment size (bp) |
| PDYE0023 | PDYE0024 | 160 |
| PDYE0023 | PDYE0025 | 135 |

This example shows that modified primers may be used for specific PCR amplification. One of the advantages of modified primers compared to non-modified primers is the ability to terminate DNA polymerase exactly at the modified nucleotide and prevent non-templated addition of a nucleotide by DNA polymerases. Another advantage is the inhibition of non-specific annealing of primers.

Example 10

Direct Sequencing of a Submicrogram Amount of Bacterial Genomic DNA

The following oligonucleotides (SEQ ID NOS: 57–58 from top to bottom) have been synthesized (length 35 bases each):
Oligonucleotides:

| Name | Sequence | position of $U^{s4}$ starting from the 3' end |
|---|---|---|
| PS822 | acggccagtgaattgtaatacgactcactataggg | none |
| FMOX-0085 | acggccagtgaattgtaatacgactcacta$U^{s4}$aggg | 5 | where $U^s$ is 2'-methylamidooxalamido- 2'-deoxyuridine. A precursor monomer $U^s$ has been modified with methylamine before the oligonucleotide synthesis. After synthesis, both oligonucleotides were deblocked and PAGE purified.

*Escherichia coli* B DNA was purchased from Amersham Pharmacia Biotech. Primers were designed for sequencing from 16S rRNA gene. The sequencing reaction contained 100 ng *E. coli* DNA, 0.1 μL ThermoFidelase 2 (Fidelity Systems, Inc.), 2 mM MgCl$_2$, 2 μL BigDye Terminator Mix (Applied Biosystems) and 10 pmole oligonucleotide. Reaction volume was 5 μL. Cycle sequencing was done at the following conditions: initial denaturation at 95° C. for 2 min, then 200 cycles with 95° C. for 5 sec, 55° C. for 30 sec and 60° C. for 2 min. After cycle sequencing was completed, samples were cooled down to 4° C. Samples were purified from non-incorporated dyes by filtration through Sephadex G-50 in 96 well filter plate (Millipore) according to the manufacturer's procedure, dried in SpeedVac system and resuspended in 3 μL loading buffer. One microliter was loaded on 5% polyacrylamide gel. Sequences were analyzed on ABI 377 sequencer.

The cycle sequencing reaction did not result in primer PS822 extension products at these conditions. The sequence reaction with FMOX0085 primer produced expected products that were detected and analyzed on automatic DNA sequencer. The readable sequence has the best match with the expected region of *E. coli* 16S rRNA gene. The longest contiguous segment of the read that did not contain errors or ambiguities was 38 bases. Out of 177 bases that were aligned with *E. coli* 16S rRNA sequence, 82% was identical.

This example shows the advantages of using modified primers in cycle sequencing reactions when the amount of template targets is very small (140,000,000 targets for FMOX0085 directed to 7 copies of 16S rRNA gene) and the size of the template is very large (4,600,000 bp for *E. coli*).

Example 11

Direct Sequencing of 60 Million Copies of Bacterial Genomic DNA

The following oligonucleotides (SEQ ID NOS: 59 and 60 from top to bottom) have been synthesized (length 32 bases each):
Oligonucleotides:

| Name | Sequence | position of $U^s$ starting from the 3' end |
|---|---|---|
| PS821 | ggtagcgactcatgagtaaaccgttcaaactg | none |
| FIME0011 | ggtagcgactcatgagtaaaccgt$U^s$caaactg | 7 | where U$^s$ is 2'-succinimido-2'-deoxyuridine. After synthesis, PS821 and FIME0011 have been reacted with Ethanolamine (modifier No. 7, Table AA).

The sequencing reaction contained 300 ng E. coli B DNA, 0.1 µL ThermoFidelase 2 (Fidelity Systems, Inc.), 2 mM MgCl$_2$, 2 µL BigDye Terminator Mix (Applied Biosystems) and 10 pmole oligonucleotide. Reaction volume was 5 µL. Thermal cycling conditions were as follows: denaturation for 2 min at 95 C., then 400 cycles with 95 C. for 5 sec and 60 C. for 1.5 min. After cycle sequencing was completed, samples were cooled down to 4° C. Samples were purified from non-incorporated dyes by filtration through Sephadex G-50 in 96 well filter plate (Millipore) according to the manufacturer's procedure, dried in SpeedVac system and resuspended in 3 µL loading buffer. One microliter was loaded on 5% polyacrylamide gel. Sequences were analyzed on ABI 377 sequencer.

The cycle sequencing reaction did not result in primer PS821 extension products at these conditions. The sequence reaction with FIME0011 primer produced expected products that were detected and analyzed on an automatic DNA sequencer. The readable sequence has the best match with the expected region of E. coli uvrB gene. The obtained sequence was aligned with E. coli uvrB gene (GenBank accession number is X03722).

(Becton Dickinson) on ice. 1 µL of pGEM-3zfp (10 ng/µL) was added to cells and mixed by tapping. Cells were incubated on ice for 30 min. Then tube was placed in water bath at 42° C. for 45 sec and immediately cooled on ice. 450 µL of S.O.C. Medium (Gibco BRL) was added. Cells were incubated at 37° C. in orbital shaker (Forma Scientific) at 225 rpm. 100 µL of cell culture was plated in Petri dish on agar containing 100 µg/ml ampicillin. Plate was incubated for 16 hours at 37° C. Individual colonies were picked and resuspended in 3 ml of LB medium containing 100 µg/ml ampicillin in 15 ml tube. Cells were grown overnight (~16 hrs) at 37 C. in shaker at 225 rpm. 50 µL of cell culture was transferred into PCR tube. Cells were pelleted by centrifugation at 2000 rpm for 5 min. Supernatant was aspirated by pipette. Cells were washed in 100 µL of 10 mM Tris-HCl (pH 8.0) then pelleted again. Supernatant was aspirated and discarded. Cell pellet was resuspended in reaction mixture, containing 0.1 µL ThermoFidelase 2 (Fidelity Systems, Inc.), 2 mM Mg Cl$_2$, 2 µL Big Dye Terminator Ready Reaction Mixture (Applied Biosystems) and 10 pmole pG5S1. Thermal cycling was as follows: denaturation for 2 min at 95° C., then 400 cycles: 95° C. for 5 sec, 55° C. for

```
FIME0011   45 tcgaagaggggctggaagangqcctggcncaccacaccttncttggggtgactgg-tcatggaaaacctt 113 (SEQ ID NO: 75)
              ||||||||||||||||||| |||||||| |||||| || || ||||| |||||||| ||| ||||||||||
Eco_uvrB  203 tcgaagaggggctggaagatggcctggcgcaccagacgttacttggcgtgactggctcagggaaaacctt 272 (SEQ ID NO: 76)
```

Out of 70 bases that were aligned with E. coli uvrB sequence, 62 (88%) were identical.

This example shows the advantages of using modified primers in cycle sequencing reactions when the amount of template targets is very small (60,000,000 targets for FIME001 directed to single copy of uvrB gene) and the size of the template is very large (4,600,000 bp for E. coli).

30 sec 60° C. for 1 min. Samples were analyzed on 36 cm 5% polyacrylamide gel on ABI PRISM 377 Sequencer.

The resulting sequence was compared to the sequence of pGEM-3zfp. Approximately 150 base good quality sequence was obtained.

```
Identities = 136/146 (93%), Positives = 136/146 (93%), Gaps = 3/146 (2%)

Query:   4  tcggaacccggggatcctctagagttcgacctgcaggcatgcaagcttgagtattctnta  63
            ||||  ||||||||||||||||||||| |||||||||||||||||||||||||||| ||
Sbjct:  15  tcggtacccggggatcctctagagt-cgacctgcaggcatgcaagcttgagtattctata  73

Query:  64  gtgttcacctaaatagcttggcngtaatnatggtcatagctgttncctgtgtgaaattgg 123
            ||||  ||||||||||||||  ||||| |||||||||||||||  ||||||||||||||
Sbjct:  74  gtgt-cacctaaatagcttggc-gtaatcatggtcatagctgtttcctgtgtgaaattgt 131

Query: 124  tatccgctcacaatancacacaacat 149 (SEQ ID NO: 77)
            ||||||||||||||| ||||||||||
Sbjct: 132  tatccgctcacaattccacacaacat 157 (SEQ ID NO: 78)
```

Example 12

Sequencing Plasmid DNA from Crude Cells

This example illustrates application of modified oligonucleotides for sequencing directly from crude cell cultures without plasmid DNA purification. E. coli cells HB101 (Gibco BRL) were transformed with plasmid pGEM-3zfp. 50 µL of cells was placed in 15 ml falcon polyethylene tube

Example 13

Sequencing Genomic DNA in Crude Cells

For sequencing from E. coli genomic DNA in crude cells the same culture was used. In this case 50 µL of cell culture was transferred into PCR tube. Cells were pelleted by centrifugation at 2000 rpm for 5 min. Supernatant was aspirated by pipette. Cells were washed in 100 µL of 10 mM Tris-HCl (pH 8.0) then pelleted again. Supernatant was discarded. Cell pellet was resuspended in 5 µL of reaction mixture containing 10 pmole FMOX0085, 0.1 µL Thermo-Fidelase 2 (Fidelity Systems, Inc.), 2 µL Big Dye Terminator Ready Reaction Mixture and 2 mM MgCl$_2$. Cycling conditions were as described above. Samples were analyzed on 36 cm 5% polyacrylamide gel on ABI PRISM 377 Sequencer. Sequence was blasted against E. coli 16S rRNA gene.

Identity score was 84%.

```
Query:     1 tactagc-attccgacttcatggagtcgagttgc-gactccaatcc-gactac-ac-cac   55
             |||||||  ||||||||||||||||||||||||| |||||||||| ||||||| || |||
rrna:   1306 tactagcgattccgacttcatggagtcgagttgcagactccaatccggactacgacgcac 1247

Query:    56 --taagagg-ccgc-tgctctcgc-aggtcg-ttctc-ttgtatgcgccattg-aacacg  107
               || |||| |||| ||||||||| ||||| ||||| |||||||||||||||  ||||
rrna:   1246 tttatgaggtccgcttgctctcgcgaggtcgcttctctttgtatgcgccattgtagcacg 1187

Query:   108 tgng-a-ccc--gcc--aaaggccatgatgactagacg-catccc  145 (SEQ ID NO: 79)
             || |  |||  |   || ||||||||||||||||| |||| ||||||
rrna:   1186 tgtgtagccctggtcgtaagggccatgatgacttgacgtcatccc  1142 (SEQ ID NO:80)
```

Example 14

Application of Fimers for SNP Detection without PCR, Directly from Genomic DNA

This example demonstrates application of timers for SNP detection directly from genomic DNA without prior PCR amplification and cloning. Since fimers have advantage in protocols involving more than 100 cycles they can be used in SNP detection. We have used ABI Prism SNaPshot ddNTP Primer Extension Kit (Applied Biosystems) for this approach. For primer extension reaction we used genomic DNA from E. coli B purchased from Amersham Pharmacia Biotech. Fimer FMOX0051 (SEQ ID NO:61) was designed for sequencing from double copy gene. Fimer FSUC0396 (SEQ ID NO: 62) was designed for sequencing from 16S rRNA gene (7 copies in E. coli).
FMOX0051 5'-gtcacgtcagtagtacggaagtagaacU$^m$gcgg-3'
FSUC0396
5'-tgacgggcggtgU$^s$gtgcaaggcccggggacgtaU$^s$tcac-3'
Where U$^m$ is 2'-methoxyoxalamido-2'-deoxyuridine, and U$^s$ is 2'-succinimido-2'-deoxyuridine. After synthesis, FMOX0051 and FSUC0396 have been reacted with Hydroxide Amine.

First primer extension reaction contained 1 µg of E. coli DNA, 10 pmole oligo FMOX0051, 0.1 µL ThermoFidelase 2 (Fidelity Systems, Inc.), 2 mM MgCl$_2$, 2.5 µL SNaPshot Ready Reaction Mix. Reaction volume was 5 µL. Control reaction contained all components except E. coli DNA. Thermal cycling conditions were: initial denaturation at 96 C. for 2 min followed by 30 cycles of denaturation at 96 C. for 10 sec, annealing at 50 C. for 5 sec and extension at 60 C. for 30 sec. After all cycles were completed samples were cooled down to 4 C. Post-extension treatment was done with 1 Unit of calf intestinal alkaline phosphatase (Pharmacia Biotech) at 37 C. for 1 hour. Phosphatase was inactivated by incubating reaction mixture at 72 C. for 15 min. Before loading sample on the gel 3 µL of reaction mixture was combined with 3 µL of loading buffer, containing 5 parts deionized formamide and 1 part 25 mM EDTA, 50 mg/ml blue dextran. Tubes were vortexed briefly and centrifuged. Samples were heated at 95 C. for 5 min then placed on ice until ready to load. One microliter from each sample was loaded on 96 lane 12 cm 10% polyacryamide gel and analyzed on ABI Prism 377 DNA Sequencer (Applied Biosystems). Data obtained from gel electrophoresis were analyzed using GeneScan Analysis Software version 3.1.

In primer extension reaction with oligo FSUC0396 amount of E. coli DNA was reduced to 50 ng. Cycling conditions were as follows: denaturation at 95 C. for 2 min, then 400 cycles with denaturation step at 95 C. for 5 sec, annealing at 50 C. for 5 sec and extension at 60 C. for 30 sec.

In both cases expected primer extension products were obtained (Table).

| Oligo | Size (nt) | Expected ddNTP | Incorporated ddNTP |
|---|---|---|---|
| FMOX0051 | 33 | ddATP | ddATP |
| FSUC0396 | 39 | ddGTP | ddGTP |

Example 15

Inibition of Primer Dimer Extension Associated with a 400-cycle Sequencing Reaction Many oligonucleotides can form dimers. This causes a problem of getting high non-specific signal in sequencing reaction. Oligonucleotide can hybridize not only to the target template but also to itself or another oligo. In this case short extension products from non-target DNA are produced in significant quantities. They can not be differentiated from short primer extension products obtained from sequencing target DNA. This makes noise signal very high at the beginning of the trace. The following example demonstrates application of oligo modifications for inhibition of primer-dimer extension reaction in DNA sequencing. Set of oligonucleotides was synthesized. FSUC0383 has no chemical modifications. FSUC0384 is degenerate oligonucleotide with no modifications. FSUC0385 has one modification in −15 position from 3'-end. FSUC0386 has two modifications: in −7 and −15 positions. U$^s$ is 2'-succinimido-2'-deoxyuridine, Y is T or C, R is A or G, N is A, C, G or T. After synthesis, oligonucleotides (SEQ ID NOS: 63–66 from top to bottom) have been reacted with Hydroxide Amine.

1. FSUC0383 5'-gatttcgcgggtggcaccgtggtgca-3'
2. FSUC0384 5'-gatttYgcgggtggNacNgtggtNca-3'
3. FSUC0385 5'-gatttYgcggg U$^s$ ggNacNgtggtNca-3'
4. FSUC0386 5'-gattTYgcggg U$^s$ ggNacNg U$^s$ ggtNca-3'

The sequencing reaction contained 1 µg E. coli B DNA, 0.1 µL ThermoFidelase 2 (Fidelity Systems, Inc.), 2 mM MgCl$_2$, 2 µL Big Dye Terminator Ready Reaction Mix (Applied Biosystems) and 10 pmole primer. Reaction volume was 5 µL. Cycle sequencing was done at the following conditions: initial denaturation at 95 C. for 2 min, then 400 cycles with 95 C. for 5 sec and 60 C. for 1.5 min. After cycle sequencing was completed samples were cooled down to 4 C. Samples were purified from non-incorporated dyes by filtration through Sephadex G-50 in 96 well filter plate (Millipore) according to the manufacturer's protocol, dried in SpeedVac system (Savant Instruments) and resuspended in 3 µL loading buffer, containing 5 parts deionized formamide and 1 part 25 mM EDTA, 50 mg/ml blue dextran. Plate was vortexed briefly and centrifuged. One microliter from each sample was loaded on 96 lane 36 cm 5% polyacryamide gel and analyzed on ABI Prism 377 DNA Sequencer (Applied Biosystems).

FSUC0383 forms several primer-dimers. One shown below can serve in sequencing reaction both as template and primer. In this case hybridization of four complementary nucleotides at 3'-end of the oligo is sufficient for extension reaction. Horizontal arrows show extension of primers. Primer sequence is shown in bold font. The following 22 base sequence is obtained: CCACGGTGCCACCCGC-GAAATC (SEQ ID NO: 81). Signal from the target DNA was low.

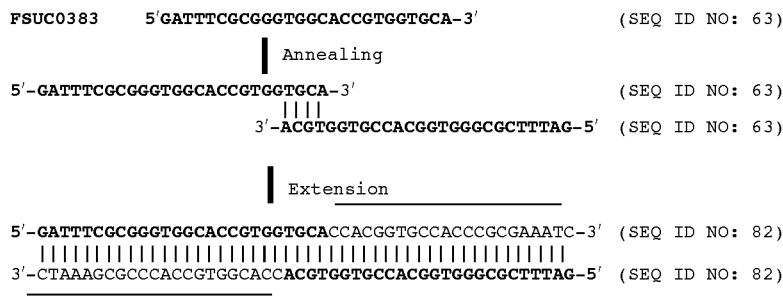

Degenerate oligonucleotides FSUC0384, FSUC0385 and FSUC0386 form similar primer dimer. Primer dimer formed by FSUC0384 also can produce in sequencing reaction 22 base sequence.

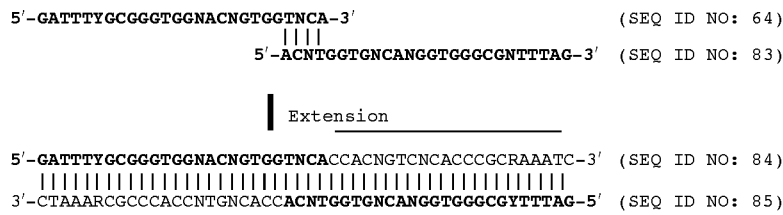

Introduction of modification in –15 position did not fully inhibit primer-dimer extension reaction. Shorter (10 base) extension products were observed.

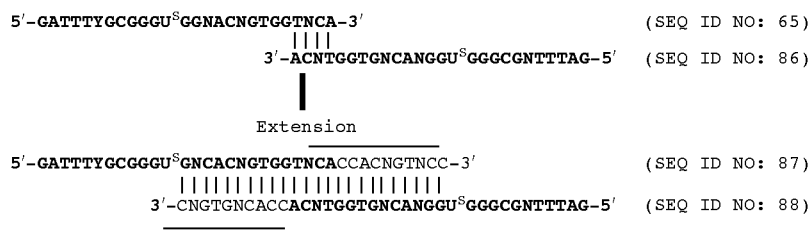

Introduction of modification in –7 and –15 positions totally inhibit primer dimer extension. In this case primer can be extended only on two bases: CC. Signal from the target DNA was significantly higher and good quality sequence was obtained.

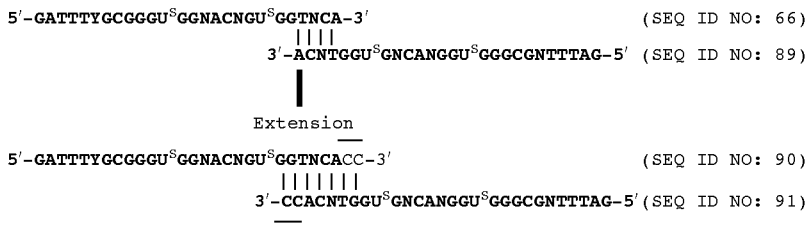

This experiment confirms that by placing a modified nucleotide in a certain position it is possible to inhibit primer dimer extension in a sequencing reaction. Thus, a non-specific signal is eliminated and a sequence from the target DNA can be read from the first nucleotide after the primer-binding site.

What is claimed is:

1. A method of inhibiting at least one molecular process involving the interaction between nucleic acids in a sample capable of undergoing said at least one molecular process, comprising:
   administering to said sample an oligonucleotide or polynucleotide containing at least one monomeric unit having formula (I):

$$A—X_n \tag{I}$$

wherein n is at least 1, A is a nucleotide or nucleoside having a ribose or deoxyribose sugar, wherein each X is attached to a carbon atom of the ribose or deoxyribose sugar, or A is not a nucleotide or nucleoside, and each X is independently selected from the group consisting of —NRCOCONu, —NHCOCR$_2$CR$_2$CONu, —NHCOCR=CRCONu, and —NHCOSSCONu, wherein each R independently represents H or a substituted or unsubstituted alkyl group, and Nu represents a nucleophile.

2. The method of claim 1, wherein said at least one molecular process is selected from the group consisting of nucleic acid hybridization and nucleic acid extension.

3. The method of claim 2, wherein said method inhibits hydridization.

4. The method of claim 3, wherein said monomeric unit decreases the melting temperature of a duplex formed between the oligonucleotide or polynucleotide and a nucleotide sequence in said sample.

5. The method of claim 3, wherein the monomeric unit prevents intramolecular hybridization within the oligonucleotide or polynucleotide.

6. The method of claim 5, wherein the oligonucleotide or polynucleotide contains at least one base complementary to the 3' terminal base and at least one said monomeric unit within 4 monomers of the complementary base.

7. The method of claim 3, wherein the monomeric unit prevents the oligonucleotide or polynucleotide from hybridizing to its duplicate to form a dimer.

8. The method of claim 7, wherein the oligonucleotide or polynucleotide contains at least one base complementary to the 3' terminal base and at least one said monomeric unit within 4 monomers of the complementary base.

9. The method of claim 2, wherein said method inhibits nucleic acid extension.

10. The method of claim 9, comprising contacting the oligonucleotide or polynucleotide with a nucleic acid strand in the sample, wherein said monomeric unit prevents a polymerase from extending the 3' end of the oligonucleotide or polynucleotide.

11. The method of claim 10, wherein the oligonucleotide or polynucleotide contains at least one said monomeric unit at any site within 4 monomers of the 3' end.

12. The method of claim 9, wherein said oligonucleotide or polynucleotide is a nucleic acid template and wherein said monomeric unit prevents extension beyond said monomeric unit.

13. The method of claim 9, wherein said oligonucleotide or polynucleotide is a template strand, further comprising:
   contacting said oligonucleotide or polynucleotide with a primer; and
   extending said primer not beyond said monomeric unit.

14. The method of claim 9, further comprising:
   contacting said oligonucleotide or polynucleotide with a template nucleic acid strand in said sample;
   extending said oligonucleotide or polynucleotide to form an extended oligonucleotide or polynucleotide;
   contacting said extended oligonucleotide or polynucleotide with a second primer; and extending said second primer not beyond said monomeric unit.

15. The method of claim 14, wherein at least one said monomeric unit is located between 4 and 9 monomers from the 3' end of said oligonucleotide or polynucleotide.

16. The method of claim 1, wherein A is not a nucleotide or nucleoside.

17. The method of claim 16, wherein A is a substituted or unsubstituted alkane, a substituted or unsubstituted cycloalkane, or a substituted or unsubstituted heterocyclic compound.

18. The method of claim 16, wherein A is a substituted or unsubstituted alkane having 3 to 100 carbon atoms, a substituted or unsubstituted cycloalkane having 3 to 12 carbon atoms in a cycle, or a substituted or unsubstituted heterocyclic compound having 3 to 20 carbon atoms in a cycle.

19. The method of claim 18, wherein A is a substituted or unsubstituted cycloalkane or heterocyclic compound having 4 to 8 carbon atoms in a cycle.

20. The method of claim 1, wherein A is a nucleotide or nucleoside having a ribose or deoxyribose sugar, wherein each X is attached to a carbon atom of the ribose or deoxyribose sugar.

21. The method of claim 20, wherein said nucleotide or nucleoside is substituted by said X at the 2' carbon of said ribose or deoxyribose sugar.

22. The method of claim 1, wherein said oligonucleotide or polynucleotide contains at least one monomeric unit having the formula (II):

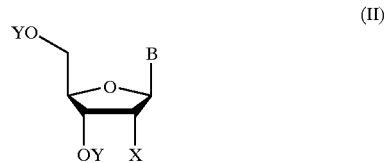

(II)

wherein B is purine or pyrimidine moiety, and each Y independently represents H, a group that protects a hydroxy group, a $(PO_3)_m^{-2}$ group wherein m is an integer of 1–3, a group reactive to link hydroxy groups, or a phosphodiester linkage to another monomer of said oligonucleotide or polynucleotide, and X is selected from the group consisting of —NRCOCONu, —NHCOCR$_2$CR$_2$CONu, —NHCOCR=CRCONu, and —NHCOSSCONu, wherein each R independently represents H or a substituted or unsubstituted alkyl group, and Nu represents a nucleophile.

\* \* \* \* \*